(12) United States Patent
Adamson et al.

(10) Patent No.: US 6,479,637 B1
(45) Date of Patent: Nov. 12, 2002

(54) HEMOGLOBIN-HAPTOGLOBIN COMPLEXES

(75) Inventors: J. Gordon Adamson, Georgetown; Jolanta Maria Wodzinska, Brampton; M. S. Celine Moore, Georgetown, all of (CA)

(73) Assignee: Hemsol Inc., Ontario (CA)

( * ) Notice: Subject to any disclaimer, the term of this patent is extended or adjusted under 35 U.S.C. 154(b) by 0 days.

(21) Appl. No.: 09/302,351

(22) Filed: Apr. 30, 1999

(30) Foreign Application Priority Data

Apr. 30, 1998 (CA) .............................................. 2236344

(51) Int. Cl.$^7$ ...................... A61K 35/14; A61K 39/385; A61K 38/16; C07K 1/00

(52) U.S. Cl. ................. 530/385; 424/193.1; 424/194.1; 514/6

(58) Field of Search ................................. 530/385, 345, 530/392; 424/193.1, 195.11, 9.2; 514/6, 2.1, 832

(56) References Cited

U.S. PATENT DOCUMENTS 5,456,908 A   10/1995   Aziz et al.
5,759,517 A   6/1998    Anderson et al.

FOREIGN PATENT DOCUMENTS

EP   0 037 388      10/1981
WO   WO 93 08842    5/1993
WO   WO 94 11399    5/1994

OTHER PUBLICATIONS

Orkin et al., Report and recommendations of the panel to assess the NIH investment in research on gene therapy, 1995, National Institutes of Health, Bethesda, MD or www.nih.gov, p. 1.*
Verma et al., Gene therapy–promises, problems and prospects, 1997, Nature, vol. 389, pp. 239–242.*
Gomez–Navarro et al., Gene therapy for cancer, 1999, European Journal of Cancer, vol. 35, No. 6, pp. 867–885.*
Tarcha et al. (1990), Polymers for Controlled Drug Delivery, Chap 14, pp. 266–273, "Beyond Today's Technology".
Carmella et al. (1990), Cancer Research, vol. 50, pp. 5453–5459, "Evaluation of CysteineAdduct Formulation in Rat Hb by 4 MethylInitroamino–1,3–Pyridyl–1–Butanone and Related Compounds".
Sakai et al. (1987), Agric. Biol. Chem., vol. 51, pp. 1921–1926, "Increase in Haptoglobin and Hp–Hb Complex in Mouse Serum After Administration of an Antitumor Agent LC–9018".

Kluger, Ronald et al., "Bioconjugation of homogeneous cross–link hemoglobin by chemical design"; Artificial Cells, Blood Substitutes, and Immobilization Biotechnology, Marcel Dekker Inc., New York, vol. 22, No. 5., (1994–11), pp. A15, XP002110925 & Proceedings of the 11$^{th}$ Congress of the Int'l Society of Artificial Cells, Blood Substitutes and Immobilization Biotechnology (ISABI); Boston, Ma, 24–27 July 1994.
Database Dissertation Abstracts [Online] University Microfilms international; De Stefano, Vittorio: "Trimesic Esters: Synthesis, Reactivity and Hemoglobin Modification"; XP002110930, vol. 35, No. 6, 1996, p. 1807; University of Toronto, CA.
Barghouthi Samira: "Interaction of the antimalarial drug primaguine with hemoglobin"; Biophysical Journal., vol. 64, No. 2, Part 2, 1993, p. A163, Abstract; Tu–Post 172 XP001076868 & Thirty–seventh Annual Meeting of the Biophysical Society; Wash., DC, Feb. 14–18, 1993.
Borissova, R. et al., "Biodegradeble Microspheres, 17, Lysosomal Degradation of Primaquine–Peptide Spacer Arms", Journal of Pharmaceutical Sciences, American Pharmaceutical Association, Wash, DC; vol. 84, No. 2, Feb. 1995; pp. 256–262, XP000541779, Abstract.
Talwar, K N. et al; "Erythrocyte based delivery system of primaquine: in vitro characterization", Journal of Microencapsulation, England, 1992 Jul.–Sep., vol. 9, No. 3, Jul./1992, pp. 357–364, XP000276769, Abstract.
Nakai, K. et al., "Inhibition of endothelium–dependent relaxation by hemoglobin in rabbit aortic strips: Comparison between acellular hemoglobin derivatives and cellular hemoglobins"; Journal of Cardiovascular Pharmacology; 1996, vol. 28, No. 1, pp. 115–123; XP002200576; Abstract.
Russo, S.F., et al; "Fluorescent probe studies of haptoglobin type 1–1"; Biochemistry, 1974, vol. 13, no. 26, pp. 5302–5304, XP001059132.
Iwashita, Y.; "Relationship between chemical properties and biological properties of pyridoxalated hemoglobin–poloxyethylene"; Biomaterials, Artificial Cells, and Immobilization Biotechnology, 1992, vol. 20, No. 2–4, pp. 299–307, XP002200577.

(List continued on next page.)

*Primary Examiner*—Deborah J. Reynolds
*Assistant Examiner*—Eleanor Sorbello
(74) *Attorney, Agent, or Firm*—Nixon & Vanderhye

(57) ABSTRACT

Construct-complexes of a hemoglobin, a hepatocyte modifying substance bound to the hemoglobin, and a haptoglobin bound to the hemoglobin, are provided, for administration to mammalian patients. The construct-complex may be formed ex vivo, or a hemoglobin-hepatocyte modifying substance combination may be administered to the patient so that haptoglobin in the mammalian body bonds thereto to form the construct-complex in vivo. Disorders of the liver may be diagnosed and treated using construct-complexes described herein.

68 Claims, 17 Drawing Sheets

OTHER PUBLICATIONS

Shim, B.S. et. al; "Study on the Natural Healing Mechanism in Tumors", Korean Journal of Bochemistry, vol. 17, No. 2, 1985, pp. 177–182, XP001075093.

Zuwala–Jagiello, J. et al; "Internalization study using EDTA–prepared hepotocytes for receptor–mediated endocytosis of haemoglobin–haptoglobin complex"; The International Journal of Biochemistry & Cell Biology; England, Aug. 1998, vol. 30, No. 8; pp. 923–931, XP00107508.

Pippard M.J., et al. "Hepatocyte iron kinetics in the rat explored with an iron chelator"; British Journal of Heamatology, England; Oct. 1982; vol. 52, No. 2, pp. 211–224, XP001075088.

Okuda, M. et al., "Expression of haptoglobin receptors in human hepatoma cells"; Biochemical Et Biophysica ACTA; Netherlands; Aug. 12, 1992; vol. 1136, No. 2; pp. 143–149, XP001075291.

Akaiwa, S.; Studies on hemoglobin metabolism main organ involved in intercellular site of hemoglobin degradation, ACTA Haematologica Japonica, 1982, vol. 45, No. 4, pp. 665–671, SP001076894.

Dobryszycka, W. et al; "Carbohydrate–mediated Catabolism of mammalian haptoglobin and haptoglobin–hemoglobin complex in the chicken"; Int'l Journal of Biochenistry; 1981; vol. 13, No. 6, pp. 739–743, XP001076893.

El Ghmati S.M. et al; "Identification of Haptoglobin as an Alternative Ligand for CD11B/CD18"; Journal of Immunology, The Williams and Wilkins Co., Baltimore, vol. 156, Jun. 1996; pp. 2542–2552, XP002915564.

Kazim, A.L. et al;"Haemoglobin binding with haptoglobin, Unequivocal demonstraton tha the beta–chains of human haemoglobin bind to haptoglobin"; The Biochemical Journal, England; Jan.. 1980; vol. 185, No. 1; pp. 285–287, XP001075092.

Yoshioka, N. et al; "Haemoglobin binding with haptoglobin, Localization of the haptoglobin–binding sites on the beta–chain of human haemoglobin by synthetic overlapping peptides emcompassing the entire chain"; the Biochemical Journal, England: Mar. 1986; vol. 234, No. 2; XP001075090.

Oshiro, S. et al; "Catabolism of hemoglobin–haptoglobin complexs in microsome subfractions"; Chemical & Phramaceutical Bulletin, Japan, Jul. 1992; vol. 40, No. 7, pp. 1847–1851, XP001077013.

Sakata, S. et al.; "Human haptoglobin binds to human myoglobin"; Biochemica Et Biophysica ACTA, Netherlands; Sep. 1986; vol. 873, No. 2; pp. 312–315, XP001075087.

Javid, J. et al; "Radio–ligand immunoassay for human hemoglobin variants"; Journal of Immunological Methods; Netherlands, 1981; vol. 41, No. 2; pp. 247–255, XP001059159.

Antonini, Eraldo et al; "Oxygen equilibrium of human hemoglobin conjugated with fluorescein isothiocyanate"; Biochim, Biophys. ACTA, 1964, vol. 82, No. 2, pp. 355–60; XP001077800.

Osada, J. et al; "Studies on the structure of haptoglobin and the haptoglobin–haemoglobin complex by spin and fluorescence labelling", ACTA Biochimica Polonica, Poland 1978, vol. 25, No. 4, 1978, pp. 333–341, XP001059134.

Kim, I.K. et al; "A novel function of haptoglobin: haptoglobin–haemoglobin complex induces apoptosis of hepatocarcinomatous Hep 3B cells"; Scandinavian Journal of Clinical and Laboratory Investigation; Norway, Oct. 1995, vol. 55, No. 6, pp. 529–535, XP001075085.

Delers, Francisco et al; "A novel and specific method for the purification of hemoglobin–binding proteins"; Anal. Biochem., 1981, vol. 118, No. 2, pp. 353–7, XP112200578.

Pshenichnaia et al. (1980), Probl. Gematol. Pereliv. Krovi (USSR), vol. 25, pp. 8–12, "Physicochemical Properties of a Complex Hb Compound With Modified Albumin".

Jia et al. (1996), Nature, vol. 380, pp. 221–226, "S–Nitrosohaemoglobin: A Dynamic Activity of Blood Involved in Vascular Control".

Perutz (1996), Nature, vol. 380, pp. 205–206, "Taking the Pressure Off".

Hoffman et al. (1990), WO 90/13645, "Production in Bacteria & Yeast of Hb and Analogues Thereof".

Houen et al. (1991), WO 91/08220, "A Method for the Stepwise, Controlled Synthesis of Chemical Species, Particularly Peptides, Coupled Products Obtained by the Method and the Use of These Coupled Products as eg as Vaccines".

Kida et al. (1991), Artificial Organs, vol. 15, pp. 5–14, "Vascular Responsiveness to Various VasoactiveSubstances After Exchange Transfusion with Pyridxylated Hb POE Conjugate (PHP) Solution in Anesthetized Rats".

Garel et al. (1982), Eur. J. Biochem., vol. 123, pp. 513–519, "Binding of 21 Thiol Reagents to Human Hb in Solution and in Intact Cells".

Abraham et al. (1984), J. Med. Chem., vol. 27, pp. 1549–1559, "Design, Synthesis, and Testing of Potential Antisickling Agents. 5. Disubstituted Benzoic Acids Designed for the Donor Site and Proline Salicylates Designed for the Acceptor Site".

Hirst et al. (1987), Radiation Research, vol. 112, pp. 164–172, "The Modification of Hb Affinity for Oxygen and Tumor Radiosensitivity by Antilipidemic Drugs".

Perutz et al., (1986), JACS, vol. 108, p. 1064–1078, "Hb as a Receptor of Drugs & Peptides: X–Ray Studies of the Stereochemistry of Binding".

Malik et al. (1980), J. Inorg. Biochem., vol. 12, pp. 317–322, "Control of Intra– & Extra–Cellular Sulphydryl–Disulphide Balances with Gold Phosphine Drugs: 31P NMR Studies of Human Blood".

Roth et al. (1981), Blood, vol. 58, pp. 300–308, "Chemical Modification of Human Hb by Antisickling Concentrations of Nitrogen Mustard".

Wodak et al. (1986), J. Biol. Chem., vol. 261, pp. 14717–14724, "Modification of Human Hb by Glutathione III Perturbations of Hb Conformation Analysed by Computer Modeling".

Craescu et al. (1986 ), J. Biol. Chem., vol. 261, pp. 14710–14716, "Covalent Binding of Glutathione to Hb II Functional Consequences and Structural Changes Reflected in NMR Spectra".

Garel et al. (1986), J. Biol. Chem., vol. 261, pp. 14704–14709, "Covalent Binding of Glutathione to Hb I Inhibition of HbS Polymerization".

Abraham (1989), Biomat. Art. Cells, Art. Organs, vol. 17, pp. 641–642, "Hb Adducts for Use as Blood Substitutes, in Blood Storage and as Anti–Ischemic Drugs".

Abraham et al. (1989), *J. Med. Chem.*, vol. 32, pp. 2460–2467, "Design, Synthesis and Testing of Potential Antisickling Agents. 7. Ethacrynic Acid Analogs".

Sinkula (1987), Ann. N.Y. Acad. Sci., vol. 507, pp. 281–288, "Some Perspectives on Targeted Delivery With Prodrugs".

Umemoto et al. (1989), Cancer Immunol. Immunother., vol. 28, pp. 9–16, "Cytotoxicities of Two Disulfide–Bond–Linked Conjugates of Methotrexate With Monoclonal Anti–MM46 Antibody".

Thorpe et al. (1987), Cancer Research, vol. 47, pp. 5924–5931, "New Coupling Agents for the Synthesis of Immunotoxins Containing a Hindered Disulfide Bond With Improved Stability in Vivo".

Raso et al. (1988), BBRC, vol. 150, pp. 104–110, "Monensin is Obligatory for the Cytotoxic Action of a Disulfide–Linked Methotrexate–Anti–Transferrin Receptor Conjugate".

Sabbioni et al. (1990), Arch. Toxicol. vol. 64, pp. 451–458, "Quantification of Hb Binding of 4,4'–Methylenebis(2–Chloroaniline) (MOCA) in Rats".

Hughes et al (1981), Biochem. J., vol. 199, pp. 61–67, "Modification of Simetryn Sulphoxide of a Specific Thiol Group in Rat Hb".

Randad et al. (1991), J. Med. Chem., vol. 34, pp. 752–757, "Allosteric Modifiers of Hb I. Design, Synthesis, Testing & Structure".

Ghose et al. (1983), Methods in Enzymology, vol. 93, pp. 280–337, "Preparation of Antibody–Linked Cytotoxic Agents".

Ziegler (1985), Ann. Rev. Biochem., vol. 54, pp. 305–329, "Role of Reversible Oxidation–Reduction of Enzyme Thiols–Disulphides in Metabolic Regulation".

Iwasaki et al. (1987), US 4 670417, "Hb Combined With a Poly(Alkylene Oxide)".

Anderson et al. (1997), US 5679777, "Hbs as Drug Delivery Agents".

Crapatureanu et al. (1999), Bioconjug Chem, vol. 10(6), pp. 1043–1802, "Molecular Necklaces, Cross–Linking Hemoglobin With Reagents Containing Covalently Attached Ligands".

Jones et al. (1993), Biochemistry, vol. 32(1), pp. 215–223, "Modification of Human Hemoglobin with Methyl Acyl Phosphates Derived From Dicarboxylic Acids".

Jones et al. (1996), J Biol Chem, vol. 271(2), pp. 675–680, "A Doubly Cross–Linked Human Hemoglobin".

Kluger et al. (1994), Artif Cells Blood Substit Immobil Biotechnol, vol. 22(3), pp. 415–428, "Cross–Linking Hemoglobin by Design: Lessons From Using Molecular Clamps".

Kuger et al. (1997), Bioconjug Chem, vol. 8(6), pp. 921–926, "Efficient Chemical Introduction of a Disulfide Cross–Link and Conjugation Site into Human Hemoglobin at Beta–Lysine–82 Utilizing a Bifunctional Aminoacyl Phosphate".

Kluger et al. (1992), Biochemistry, vol. 31(33), pp. 7551–7559, "Three–Point Cross–Linking: Potential Red Cell Substitutes From the Raction of Trimesoyl Tris(Methyl Phosphate) With Hemoglobin".

Schumacher et al. (1995), Nature, vol. 375(6526), pp. 84–87, "Allosteric Transition Intermediates Modelled by Crosslinked Haemoglobins".

Schumacher et al. (1997), Proc Natl Acad Sci USA, vol. 94(15), pp. 7841–7844, "Allosteric Intermediates Indicate R2 is the Liganded Hemoglobin End State".

Ueno et al. (1986), J Chromatogr, May 30, pp. 359193–359201, "Methyl Acetyl Phosphate: A Novel Acetylating Agent".

Ueno et al. (1986), Arch Biochem Biophys, vol. 244(2), pp. 795–800, "Site–Specific Modification of Hemoglobin by Methyl Acetyl Phosphate".

Mahieu (1993), Int J Biol, vol. 15, pp. 233–240, "Reactivity of 42 Disulfides With Thiol Group of Human Haemoglobin and Human Serum Albumin".

Garel et al. (1984), Mol Pharmacol, vol. 26(3), pp. 559–565, "Inhibition of Erythrocyte Sickling by Thiol Reagents".

Patwa et al. (1987), Blood Cells, vol. 12(3), pp. 589–601, "Design, Synthesis, and Testing of Potential Antisickling Agents. 6. Rheologic Studies With Active Phenoxy and Benzyloxy Acids".

Talwar et al. (1992), J Microencapsulation, vol. 9(3), pp. 357–364, "Erythrocyte Based Delivery System of Primaquine: In Vitro Characterization".

Wootton (1984), FEBS Lett, vol. 171(2), pp. 187–191, "Analysis of the Effect of Benzafibrate on the Oxygen Dissociation curve of human hemoglobin".

Horvath et al. (1974), Int J Radiat Biol, vol. 25, pp. 351–359, "Haemoglobin, a Sulphhydryl–Protein in the Binding Reaction With Radioprotective MEG".

Benesch et al. (1982), Biochem Biophys Res Commun, vol. 106, pp. 1359–1363, "The Binding of Folyl Polyglutamates by Hemoglobin".

Bhattacharyya et al. (1990), Biochem Biophys Res Commun. vol. 167, pp. 1146–1153, "Evidence for Cooperative Binding of Chloropromazine With Hemoglobin: Equilibrium Dialysis, Fluorescence Quenching and Oxygen Release Study".

Ascenzi et al. (1999), Biochem Mol Biol Int, vol. 47(6), pp. 991–995, "Stabilization of the T–State of Human Hemoglobin by Proflavine, an Antiseptic Drug".

Garel et al. (1990), Biochimica et Biophysica Acta, vol. 1041, pp. 133–140, "Changes of Polymerization and Conformation of Hemoglobin S Induced by Thiol Reagents".

\* cited by examiner

HEMOGLOBIN-HAPTOGLOBIN COMPLEXES

FIELD OF THE INVENTION

This invention relates to protein complexes and use thereof in medical applications. More specifically, it relates to complexes of hemoglobin compounds with therapeutic substances such as drugs, genes etc. which have a therapeutic action on specific parts and/or organs of the body, and means for targeting such complexes to specific body parts and body organs. Also within the scope of the invention are complexes of hemoglobin with diagnostic substances, such as imaging agents.

BACKGROUND OF THE INVENTION AND PRIOR ART

The use of hemoglobin and modified hemoglobin as a drug delivery means has been proposed previously. Hemoglobin, as a natural component of red blood cells, present and circulating throughout the body in relatively large quantities, has well-established bioacceptability and the potential-to deliver drugs throughout the body.

Thus, Kluger et al., U.S. Pat. No. 5,399,671 describe a hemoglobin compound which has been cross-linked to effect intramolecular stabilization of the tetrameric structure thereof, but which contains a residual functional group on the cross-linker residue to which drugs for delivery can be covalently attached.

Anderson et al., U.S. Pat. No. 5,679,777, describe complexes of hemoglobin compounds and polypeptide drugs, in which the polypeptide drug is bound to a globin chain through a disulfide linkage to a cysteine unit inherent in or genetically engineered into the globin chain.

Haptoglobins (Hp) constitute part of the $\alpha_2$-globin family of serum glycoproteins. Haptoglobins are present in mammalian plasma, and constitute about one-quarter of the $\alpha_2$-globulin fraction of human plasma. Each individual has one of three phenotypic forms of haptoglobin, of close structural and chemical identity. Haptoglobins are composed of multiple $\alpha\beta$ dimers and the phenotypes are conventionally denoted Hp 1-1, Hp 2-1 and Hp 2-2. The $\beta$ chains are identical in all haptoglobin phenotypes, but the $\alpha$ chains vary ($\alpha^1$ and $\alpha^2$). The amino acid sequences of all chains are known. Hp 1-1 is composed of two $\alpha^1\beta$ dimers and has a molecular weight of about 98 kDa. The structure of Hp 2-1 and Hp 2-2 can be written as follows: $(\alpha^1\beta)_2(\alpha^2\beta)_n$ where n=0,1,2, ... and $(\alpha^2\beta)_m$ where m=3,4,5, ... respectively.

Delivery of drugs to a patient suffering from a disease or disorder affecting primarily one body part or one body organ is best accomplished by choosing a delivery method which targets the part or organ in need of treatment with a high degree of specificity. Such a delivery system makes most effective use of the active drug, so as to reduce the necessary dosage level, and reduces side effects of the drug.

One function of haptoglobin is to bind extracellular hemoglobin, arising from red blood cell lysis, to form essentially irreversible haptoglobin-hemoglobin complexes which are recognized by specific receptors on hepatocytes in the liver. In this way, hemoglobin is targeted to the liver for metabolism.

Control and manipulation of genes and gene products are potentially powerful means of treating various diseases and genetic disorders. When specifically introduced into the cells, genes can use the host cell biosynthetic machinery for the expression of the therapeutic biomolecules they encode. For successful gene therapy, one must devise a successful method of in vivo gene delivery. One such technique developed in recent years is receptor-mediated delivery. This has the advantage of high specificity of delivery to the cells which express the targeted receptor.

The specific targeting of low molecular weight therapeutic and diagnostic agents to tissues is enhanced greatly through the use of receptor-mediated delivery. Diagnostic agents such as fluorescent or radiolabeled substances indicate the location and quantity of cells bearing the targeted receptors when such agents are administered as complexes with ligands for those receptors. These complexes are also useful in characterizing the binding and transport properties of receptors on cells in culture. Such information is useful in detection of and/or design of therapy for tissues containing the cells being recognized, either in vitro or in vivo.

SUMMARY OF THE INVENTION

It is an object of the present invention to provide a means and composition for specifically targeting hepatocytes or other cells having receptors for hemoglobin-haptoglobin complexes with therapeutically active substances or diagnostic agents.

It is a further object of the present invention to provide a novel complex of a substance selected to exert a beneficial effect on a mammalian patient's liver, in vivo, and a substance which specifically targets hepatic cells.

The present invention describes haptoglobin-hemoglobin construct-complexes to which hepatocyte-modifying agents are attached. Such haptoglobin-hemoglobin construct-complexes serve as effective hepatocyte-targeting vehicles for the attached agents, for delivery of specific hepatocyte-modifying agents (drugs, diagnostics, imaging compounds, etc) to the liver, and to other cells having the appropriate hemoglobin-haptoglobin receptors.

The expression "construct-complex" is used herein to refer to the combination of haptoglobin with hemoglobin to which a bioactive, therapeutic or diagnostic agent is attached. The present invention provides construct-complexes composed of a hemoglobin compound, a haptoglobin and a hepatocyte-modifying substance of interest such as a drug, a diagnostic agent or a gene. In one aspect of the present invention, the construct-complex is prepared extracorporeally and then administered to the patient. In another aspect, a complex of hemoglobin-hepatocyte modifying substance is prepared extracorporeally, administered to the patient, and forms the construct-complex of haptoglobin-hemoglobin-hepatocyte modifying substance with haptoglobin which is naturally present in the patient's serum. In a further aspect, the patient's haptoglobin level may be supplemented by haptoglobin administration, a known procedure, either before, during or after administration of the hemoglobin-hepatocyte modifying substance-construct-complex. In any case, the construct-complex specifically targets and binds as a ligand to the hepatocyte receptors, owing to the presence of the haptoglobin and hemoglobin portions of the construct-complex.

The construct-complexes of the present invention, formed ex vivo or in vivo, target any cells having receptors for Hb-Hp complexes, and this includes metastases arising from primary hepatoma. It is normally difficult to identify and treat metastases because of the systemic distribution and small size of such cancers. Secondary hepatic metastases, i.e. hepatoma cells outside the liver which have such receptors are targeted by the construct-complexes of the present invention, as well as cells of the liver, and should be regarded as "hepatocytes" as the term is used herein.

Further, the construct-complexes of the present invention may exert beneficial effects on neighboring cells, if the hepatocyte modifying substance is, for example, a drug which is active towards neighboring cells even if they are not hepatocytes. They may also modulate or initiate the activity of other therapeutic or diagnostic agents delivered by other methods for hepatocyte modification, such as prodrugs, enzymes or genes coding for enzymes and requiring activation to cause an effect. Agents effecting such action resulting in hepatocyte modification or effect on other agents or cells are hepatocyte modifying agents according to this invention.

The construct-complex according to the present invention can be generally represented by the formula:

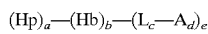

$$(Hp)_a-(Hb)_b-(L_c-A_d)_e$$

where
  a=1 to about 10;
  b=0.5 to about 10;
  c=0 to about 10;
  d=1 to about 20;
  e=1 to about 20;
  Hp is haptoglobin as described herein;
  Hb is a hemoglobin as described herein;
  L is a linker as described herein; and
  A is a hepatocyte modifying agent as described herein, in which the stoichiometry of Hp to Hb in the complex is dictated by the available number of binding sites on the two proteins, but is generally of the order of 1:05 to 1:2.

BRIEF REFERENCE TO THE DRAWINGS

FIG. 1 is a reaction scheme illustrating diagrammatically a process for producing one embodiment of a construct-complex of the present invention;

FIG. 2. Panels A, B, C, and D are size exclusion chromatography results, in the form of plots of absorbance at 280 nm and 414 nm against elution time, indicating the molecular weight distribution of the four products of Example 2. Complexes were formed using poly(L-lysine) of molecular weight (A) 4 kDa, (b) 7.5 kDa, (C) 26 kDa and (D) 37 kDa.

Figure 10:
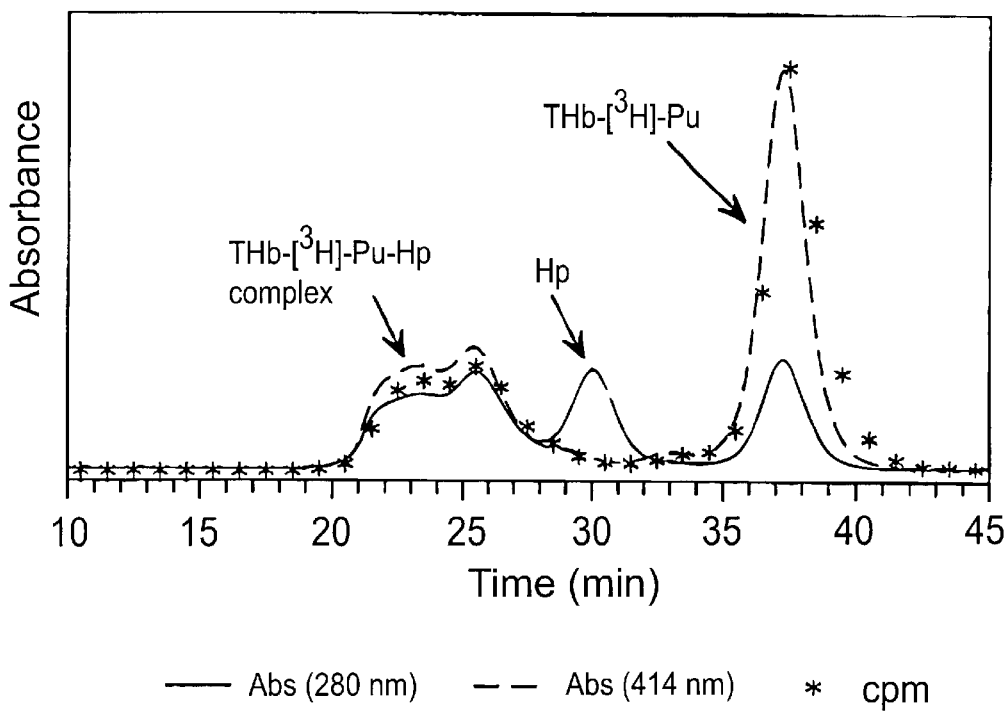
Figure 11:
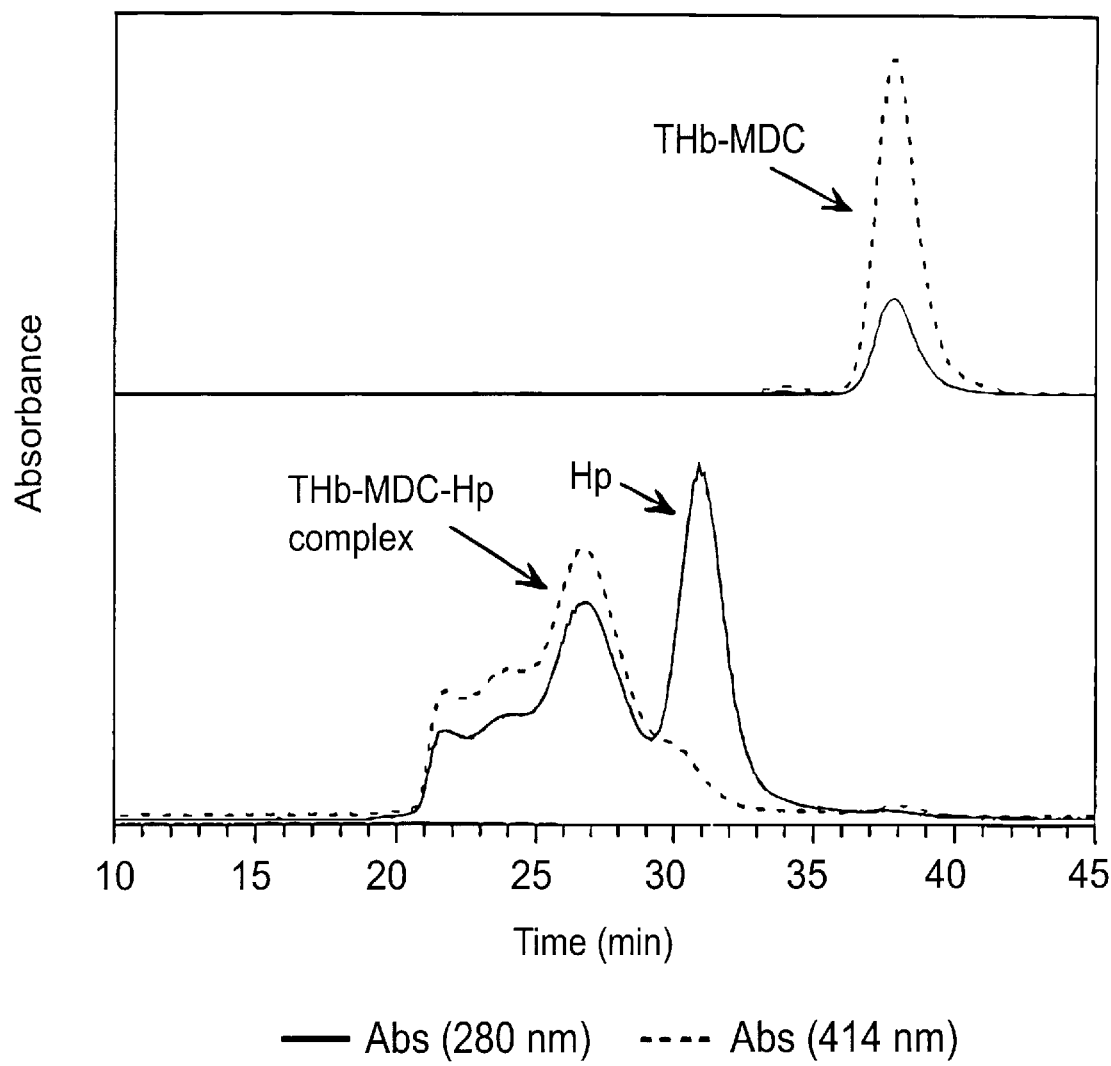
Figure 12:
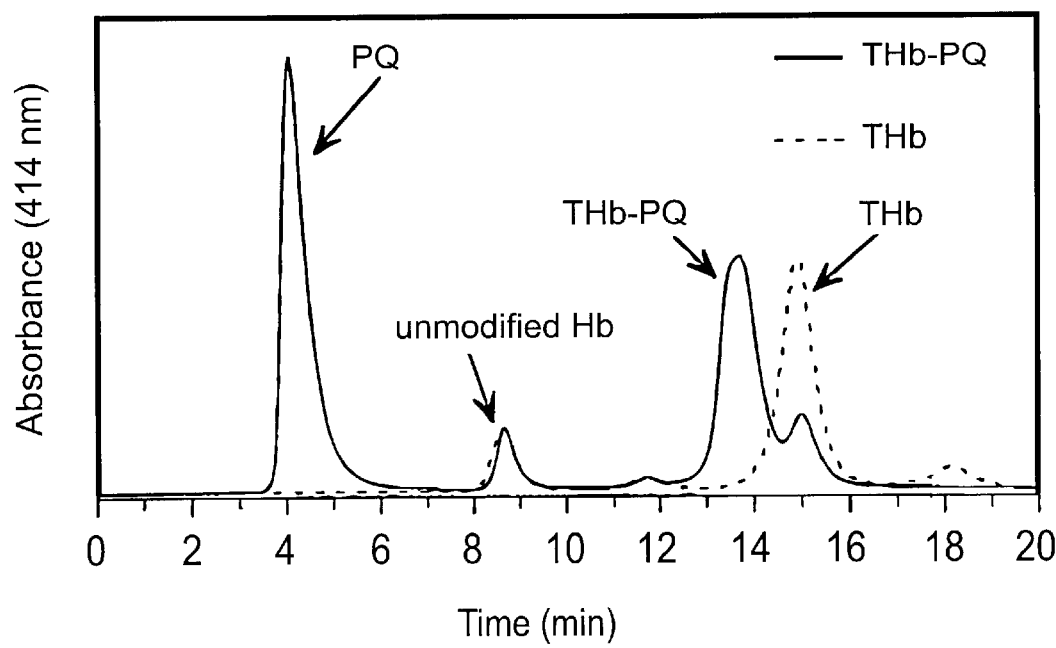
Figure 13:
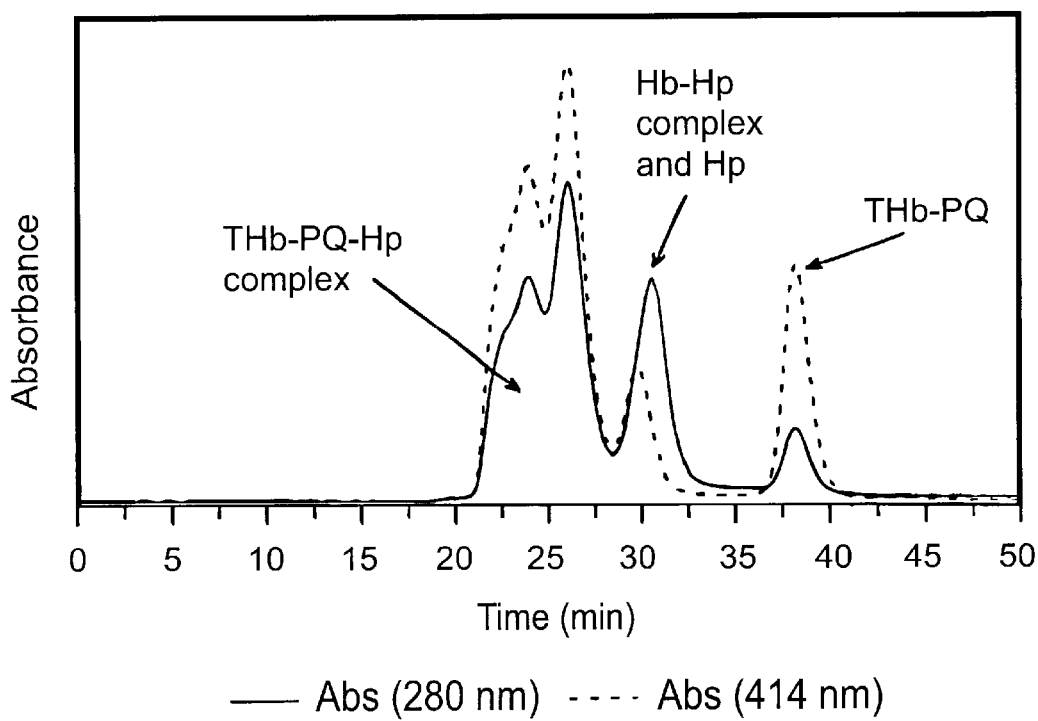
Figure 14:
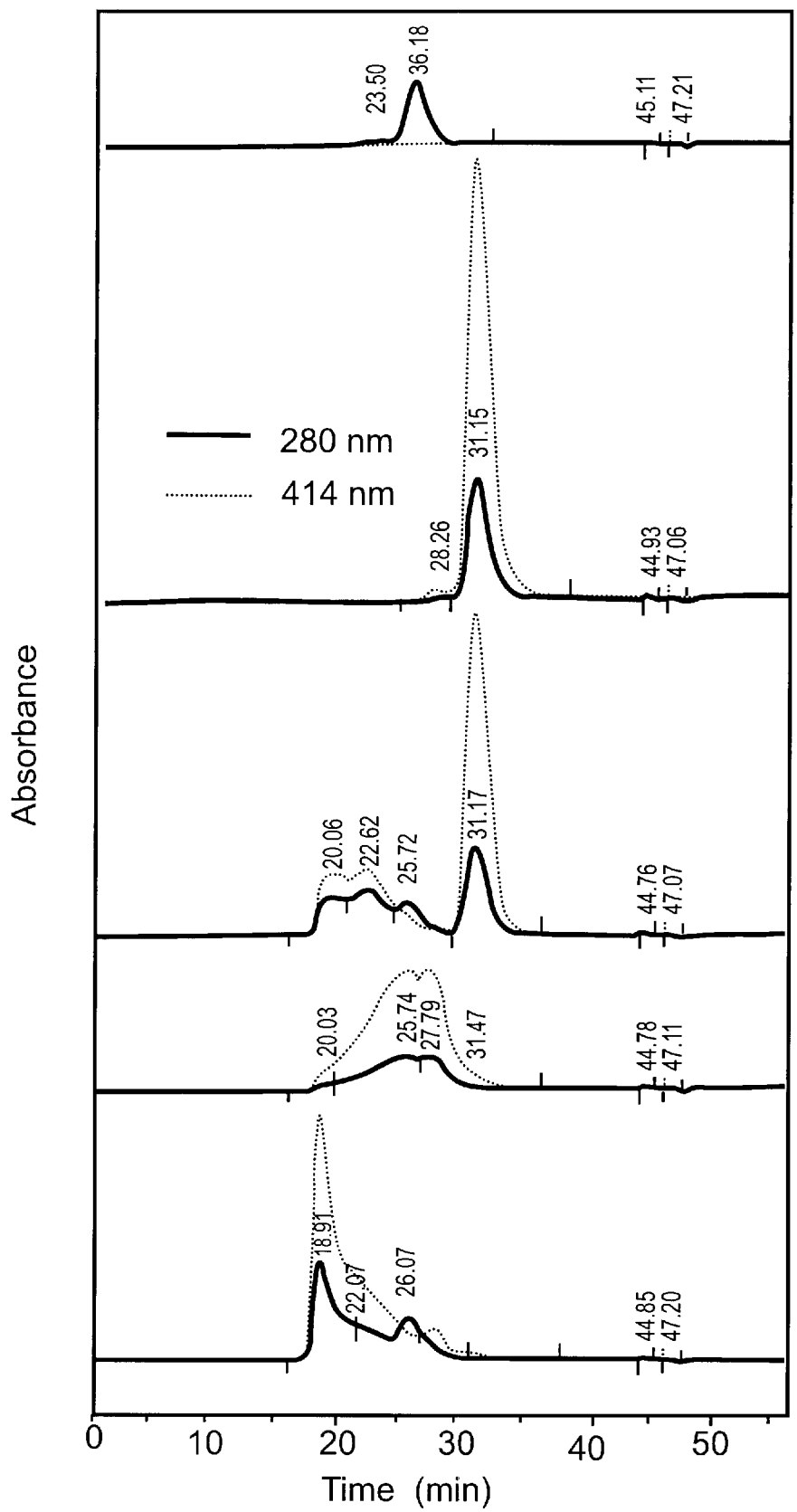

FIG. 9. Panels A, C and D show size exclusion chromatograms of the products of Example 9, utilizing (A) haptoglobin 1-1, (C) haptoglobin 2-1, (D) haptoglobin-2-2;

Panel B shows the UV-visible spectra of the products of Example 9;

FIG. 10 is a size exclusion chromatogram of the product of Example 11;

FIG. 11 is a size exclusion chromatogram of the product of Example 13;

FIG. 12 shows anion exchange chromatograms (overlaid) of products and starting materials of Example 14;

FIG. 13 shows overlaid size exclusion chromatograms of the products of Example 15;

FIG. 14 shows size exclusion chromatography elution profiles with detection at 280 (solid lines) and 414 nm (broken lines) for products of Example 16; (A) haptoglobin 1-1, (B) 64 kDa ORHb, (C) haptoglobin-[64-kDa ORHb], (D) >64 kDa ORHb, (E) haptoglobin-[>64 kDa ORHb].

Figure 15:
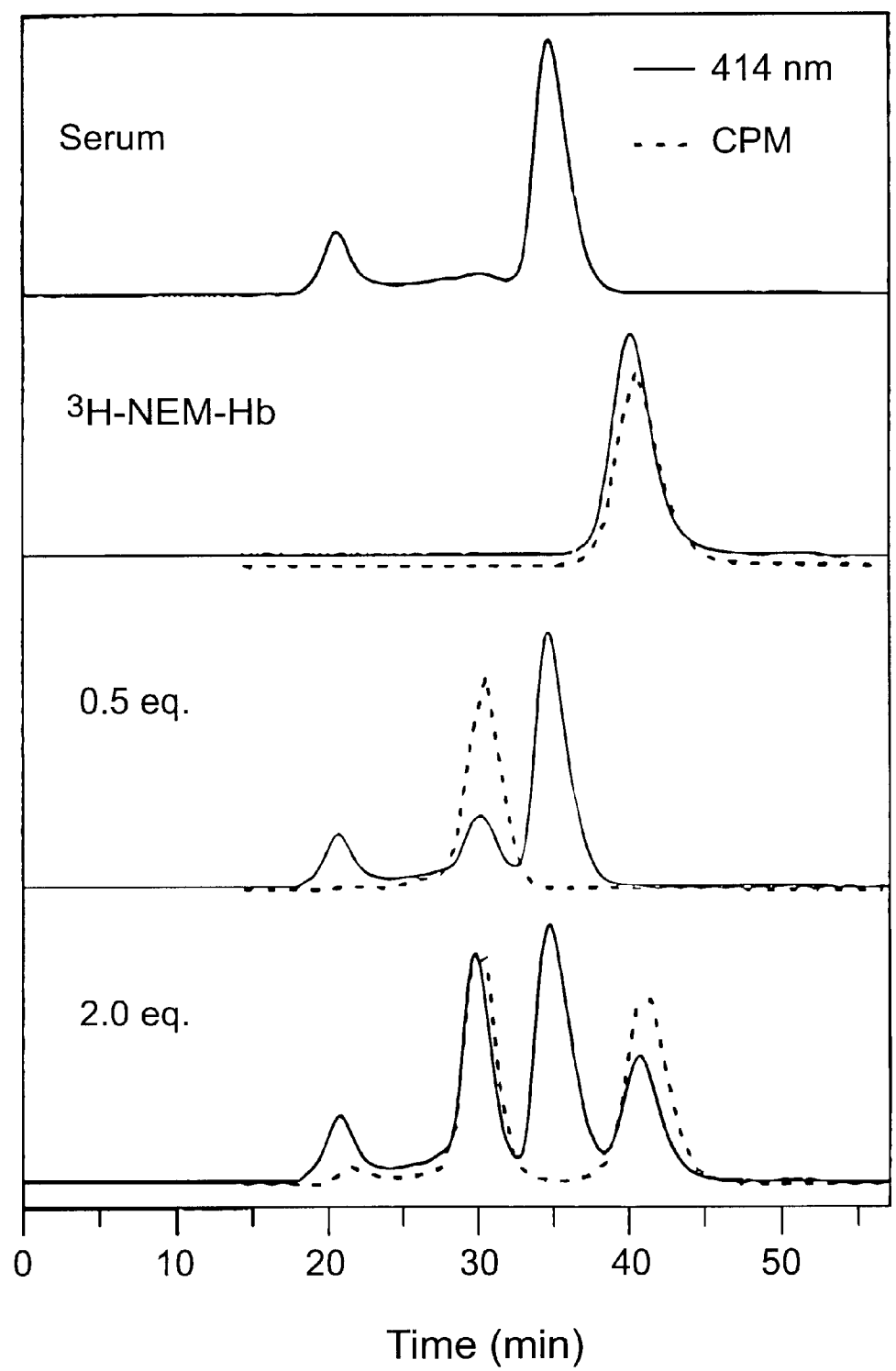
Figure 17:
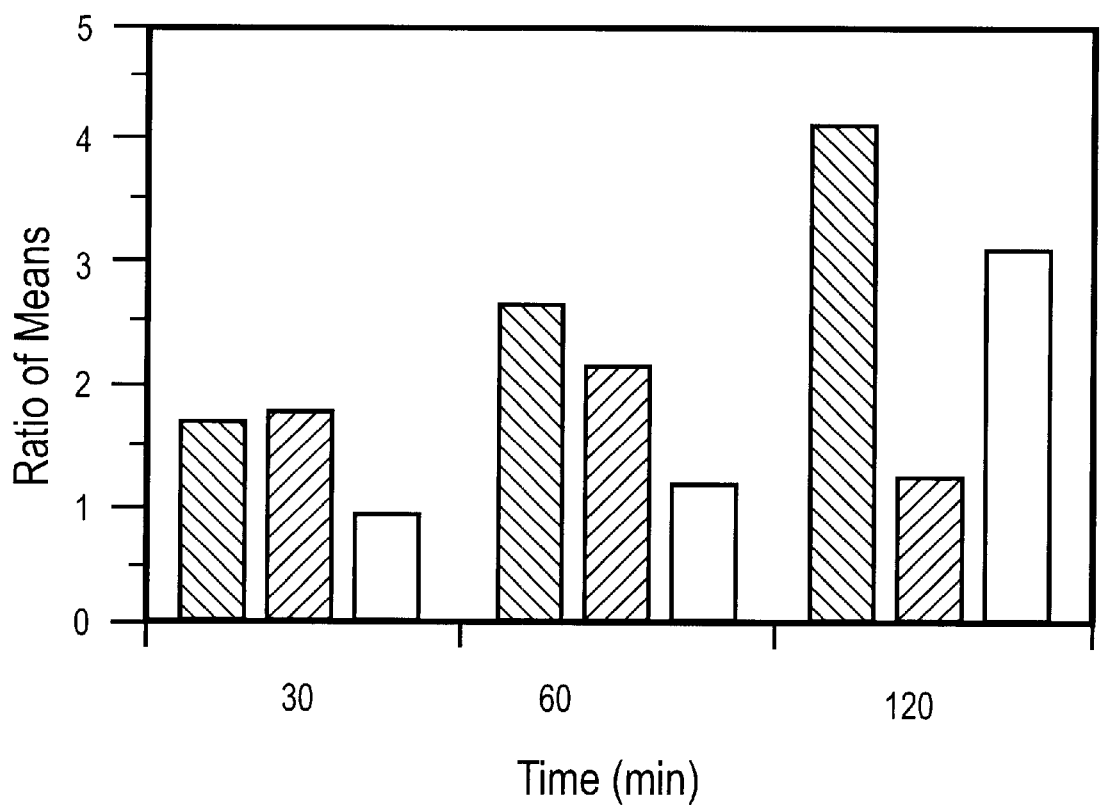

FIG. 15 shows size exclusion chromatograms of products of Example 17;

FIG. 16. Panels A–D are graphical presentations of analyses of results obtained in Example 18;

FIG. 17 is a graphical presentation of further analyses of results obtained according to Example 18.

DESCRIPTION OF THE PREFERRED EMBODIMENTS

A wide range of hepatocyte modifying substances may be used in complexes of the present invention. These can be therapeutic agents, diagnostic agents, markers or the like capable of interacting with hepatocytes and consequently capable of acting in vivo at the liver. They can be designed for treatment of normal liver cells or such cells undergoing metastases. Thus, the hepatocyte-modifying substances can be antineoplastic substances (doxorubicin, daunorubicin, ricin, diphtheria toxin, diphtheria toxin A, for example), antiviral substances (ara-AMP, trifluorothymidine, interferon, antisense oligonucleotides, ribavirin, cytarabin, acyclovir, didonosine, vidarabine, adefovir, zalcitabine, lamivudine, fialvridine, and other nucleoside analogs, for example), anti-inflammatory substances, anti-parasitic substances, antimicrobial substances, antioxidant substances, hepatoprotective agents, imaging and diagnostic agents, nucleic acids and their compounds for effecting gene therapy, agents effecting lipid metabolism, anti-toxicants, proteins, enzymes, enzyme and prodrug combinations, and the like.

Examples of diagnostic agents useful in construct-complexes in this invention include radiolabeled lysine and putrescine, and the fluorescent compounds monodansyl cadaverine and fluorescein. Low molecular weight therapeutic agents can also be selectively targeted to the cells to minimize side effects at non-targeted tissues and vascular clearance. Examples of therapeutic agents in this application include putrescine, a modulator of cell growth and activity, and primaquine, an anti-malarial substance.

More specifically, hepatocyte modifying substances which can be used in construct-complexes according to the present invention include agents for treating or preventing hepatic fibrosis, a dynamic process from chronic liver damage to cirrhosis, and for treating or preventing other chronic liver disorders including viral hepatitis and alcoholic and cryptogenic liver diseases. These hepatocyte modifying substances include cytoprotective drugs such as S-adenosyl-L-methioine, prostaglandin E1,E2,I2 and their analogues, colchicine and silymarin, all of which have been demonstrated to be effective in protecting the liver from damage and having anti-fibrotic properties. Other liver protectant substances which are hepatocyte modifying substances within the scope of this invention include free radical scavengers/anti-peroxidants such as glutathione, SA 3443 (a cyclic disulphide), S-adenosylmethionine, superoxide dismutase, catalase, α-tocopherol, vitamin C, deferoxamine, (+)cianidanol-3, mannitol, tryptophan, pantetheine, pantotheinic acid, cystamine, cysteine, acetylcysteine, folinic acid, uridine monophosphate, zinc sulphate, schizandrin B and kopsinine; lipoxygenase inhibitors such as the aforementioned prostaglandins and their analogs dimethyl PGE, misoprostol and enisoprost, and prostacyclin PGI2 and its analog iloprost; calcium channel blockers such as trifluoroperazine, verapamil, nifedipine and related dihydropyridine compounds, and dilitiazem; proteinase inhibitors; atrial natriuretic peptide; $\alpha_2$-macrofetoprotein;synthetic linear terpenoid; putrescine; cholestyramine; ε-aminocaproic acid,; phenylmethylsulfonyl fluoride; pepstatin; glycyrrhizin; fructose 1,6-biphosphate; and ursodeoxycholic acid.

The hemoglobin compound useful as a component of the complexes of the present invention can be substantially any hemoglobin compound providing the necessary degree of biocompatibility for administration to a patient or animal, the necessary sites for attachment of the hepatocyte modifying substance of interest, and having sufficient binding affinity for haptoglobin. Within these limitations, it can be a naturally occurring hemoglobin from human or animal sources. It can be a modified natural hemoglobin, e.g. an intramolecularly cross-linked form of hemoglobin to minimize its dissociation into dimers, an oligomerized form or a polymerized form. It can be a hemoglobin derived from recombinant sources and techniques, with its naturally occurring globin chains or such chains mutated in minor ways. It can be comprised of subunits or fragments of Hb, or derivatives thereof, which have affinity for haptoglobin. It can be a hemoglobin in which individual amino acids of the globin chains have been removed or replaced by site specific mutagenesis or other means. Certain modifications which are known to decrease the affinity of hemoglobin for binding to haptoglobin are preferably avoided in hemoglobin compounds used in the present invention.

One type of preferred hemoglobin compounds are those which comprise hemoglobin tetramers intramolecularly cross-linked to prevent their dissociation into dimers, and which leave functional groups available for chemical reaction with the hepatocyte modifying substance, either directly or through a chemical linker molecule. Such hemoglobin compounds have the advantage that they provide a known, controlled number of reactive sites specific for the therapeutic substance of interest, so that an accurately controlled quantity of the therapeutic substance can be attached to a given amount of hemoglobin compound. They also have the added advantage that they avoid utilizing sites on the globin chains for linkage to the therapeutically active substance, so as to minimize conformation disruption of the globin chains and minimize interference with the hemoglobin-haptoglobin binding and with binding of the construct-complex to the receptor protein on a hepatocyte cell.

Human hemoglobin, e.g. that obtained from outdated red blood cells, and purified by the displacement chromatography process described in U.S. Pat. No. 5,439,591 Pliura et al. is one preferred raw material for preparation of the hemoglobin product for use in the complex of the present invention. This material may be cross-linked with a trifunctional cross-linking agent as described in aforementioned U.S. Pat. No. 5,399,671, Kluger et al., namely a reagent which utilizes two of its functional groups for intramolecular cross-linking between subunits of the hemoglobin tetramer, and leaves its third functional group available for subsequent reaction with a nucleophile. A specific example of such a cross-linking reagent is trimesoyl tris(3,5-dibromosalicylate), TTDS, the chemical formula of which is given in the attached FIG. 1, and the preparation of which is described in the aforementioned Kluger et al. U.S. Pat. No. 5,399,671.

When cross-linked hemoglobin, i.e. stabilized tetrameric hemoglobin is used as a component of the complex, the hepatocyte modifying substance is bound to the hemoglobin, either directly or through a chemical linker or spacer, and then this complex may be administered to the patient so that the haptoglobin-hemoglobin binding takes place in vivo. The entire construct-complex, (haptoglobin-hemoglobin-hepatocyte modifying substance) can, if desired, be formed extracorporeally and then administered to the patient, and this can under some circumstances lead to better control of the amounts of active substance finally being delivered to the hepatocytes. However, such a procedure is not normally necessary, save for those exceptional patients having zero or low levels of haptoglobin, e.g. in conditions of acute hemolysis. Such patients can be administered haptoglobin before, during and/or after administration of the construct-complex of the invention. Usually, however, there is sufficient haptoglobin in the patient's plasma to form the construct-complex in situ and effect its delivery to the hepatocytes. Preparation of the two-part complex and administration of that to the patient, to form the three-part complex in situ is generally cheaper and less complicated.

Use of intramolecularly crosslinked hemoglobins will give rise to high molecular weight polymers containing more than one hemoglobin and/or haptoglobin owing to the presence of two binding sites on each of these proteins. There may be advantages to using non-crosslinked hemoglobin as a component of the construct-complexes of the present invention. Such a hemoglobin, with a hepatocyte-modifying substance bound to it, will dissociate into dimeric hemoglobin of approximate molecular weight 32 kDa, and two such dissociated dimeric hemoglobin products bind to a single molecule of haptoglobin to give a complex according to the present invention. The formation of high molecular weight haptoglobin-hemoglobin complexes is thus avoided. Haptoglobin binding to αβ-dimers is generally a much faster reaction than haptoglobin binding to crosslinked hemoglobin. The lower molecular weight complexes resulting from the use of non-crosslinked hemoglobin may show improved hepatocyte receptor binding and uptake.

Where hemoglobin of a form which will dissociate into dimers is used as a component of the present invention, or where hemoglobin dimers themselves are used, for example, where the dimers have been modified such that they cannot reform 64 kba hemoglobin, it is preferred to form the construct-complex according to the invention extracorporeally, and then to administer the finished construct-complex to the patient, so as to avoid the risks attendant on administering to the body a molecular species of too small a molecular weight, namely, clearing the drug too rapidly through excretion. Administration of Hb dimers bearing therapeutic or diagnostic agents may be possible without prior binding to haptoglobin in cases where complex formation in vivo is adequate prior to clearance of the modified dimer.

A further example of a hemoglobin compound useful in construct-complexes of the present invention is dimeric hemoglobin bearing a modifying group containing thiol, preferably a terminal side chain thiol, of the type described in U.S. Provisional Patent Application of Kluger and Li, entitled "Hemoglobin With Chemically Introduced Disulfide Crosslinks and Preparation Thereof", filed Nov. 3, 1997. Hepatocyte modifying substances can be ligated to such dimeric hemoglobin, either by direct reaction with the exposed thiol, or by direct reaction with an activated form of the thiol, or by mixed disulfide formation, or through a linker molecule. Construct-complexes of this type are made extracorporeally and administered to a patient in this form. The hemoglobin-hepatocyte modifying substance conjugate can also be administered for in vivo Hp binding. The use of dissociable hemoglobin (32 kDa molecular weight) has the advantage over the use of cross-linked hemoglobin tetramers in that they provide an exposed dimer-dimer interface which facilitates haptoglobin binding.

The construct-complexes of the present invention may also utilize hemoglobin which has been modified in a manner which results in impaired nitric oxide binding. Such modified hemoglobins are known in the art. Reduced NO binding may reduce the tendency of the hemoglobin to effect modifications to a patient's blood pressure upon administration, an effect which has been noted with some hemoglobins, even in small amounts.

In forming the construct-complex, it may be necessary to interpose between the reactive site on the hemoglobin chosen and the hepatocyte modifying substance, a chemical linker or a spacer group. This depends upon the nature of the available chemical group on hemoglobin for linking, and on the chemical groups available on the hepatocyte modifying compound, for this purpose. For example, a polycationic segment such as polylysine is appropriately attached to the electrophilic site of the TTDS modified hemoglobin to provide a binding site for DNA through electrostatic interactions. Linear polymers of lysine provide appropriate cationic segments for this purpose.

A construct-complex according to a preferred embodiment of the present invention comprises a haptoglobin molecule, which may be haptoglobin 1-1 or any other phenotype, bonded to one or more molecules of a hemoglobin compound by means of strong non-covalent interaction. The hemoglobin may be cross-linked, oligomerized or unmodified, as described above.

Figure 1:
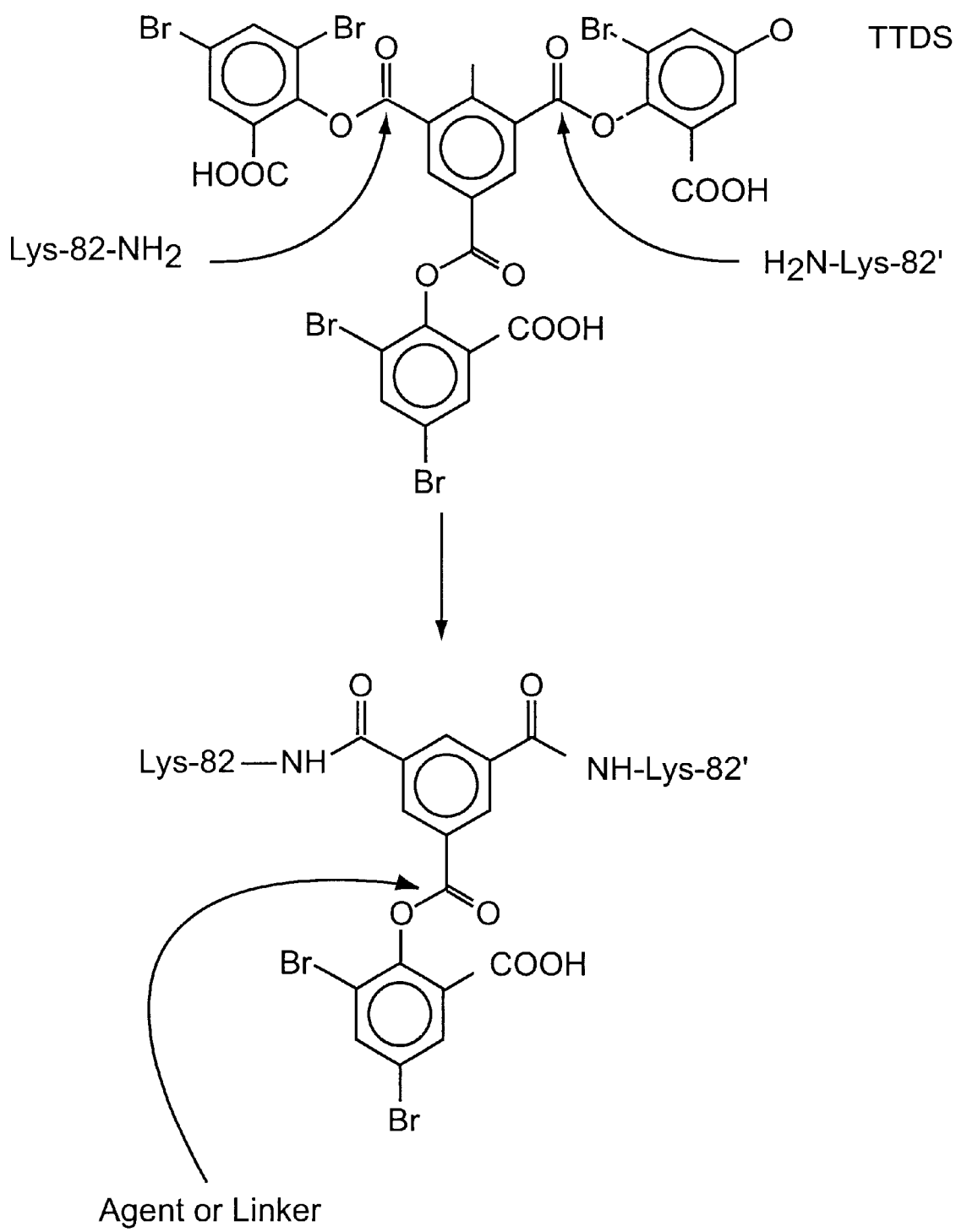

FIG. 1 diagrammatically illustrates the chemical steps involved in preparing a cross-linked hemoglobin, for reaction with a linker and/or agent, and with haptoglobin to form a construct-complex according to various embodiments of the invention. TTDS is reacted with hemoglobin, whereupon two of the three 3,5-dibromosalicylate groups leave. Primary amine groups at Lys-82 and β-Lys-82 on the hemoglobin are bonded by an amide linkage to the cross-linker, forming an intramolecularly cross-linked and stabilized tetrameric hemoglobin with the third dibromosalicylate group intact and available for further reaction. In the second step, the cross-linked hemoglobin is reacted with the agent or a linker (in the case of Example 1, polylysine) necessary for later attachment of the agent. In other cases, the hepatocyte modifying substance, or active agent, takes the place of the polylysine in the scheme of FIG. 1, to form the construct. The complex is then ready for administration to the patient to form a construct-complex in situ, or alternatively haptoglobin can be reacted with the complex so formed extracorporeally, so that the haptoglobin binds to the hemoglobin portion of the complex to form the three part complex ready for administration to the patient. Alternatively, the TTDS-modified hemoglobin with a linker attached can be reacted with haptoglobin and agent attached as a final step. After administration, the construct-complex will bind to the hepatocytes, where the haptoglobin-hemoglobin mediates binding to the selective receptors thereof and allows the hepatocyte-modifying substance to be delivered to and enter into the hepatocyte utilizing the hepatocyte receptors selective for haptoglobin-hemoglobin complex.

SPECIFIC EXAMPLES

Example 1

Conjugation of TTDS Cross-linked Hemoglobin (THb) to Poly(L-lysine)

Poly(L-lysine) conjugates of TTDS cross-linked hemoglobin (THb-$K_n$) were synthesized by adding poly(L-lysine) to THb-DBS (TTDS cross-linked hemoglobin with one unhydrolyzed 3,5-dibromosalicylate functionality) at 1:1 molar ratio to promote formation of conjugates in which only one molecule of hemoglobin is attached to a single poly(L-lysine) chain. The poly(L-lysine) used in this experiment is a linear polymer with an amide linkage between the carboxyl group and the α-amino group of lysine. Polymers with an average molecular weight of 4 kDa ($K_{4kDa}$), 7 7.5 kDa ($K_{7.5kDa}$), 26 kDa ($K_{26kDa}$) and 37 kDa ($K_{37kDa}$) were conjugated to THb.

TTDS (13.9 mg) in ethanol (100 µL) was added to deoxyhemoglobin (5 mL, 8.5 g/dL) in 50 mM borate pH 9.0. The reaction mixture was stirred at 30° C. under nitrogen for 45 min. The hemoglobin was then charged with CO (the solution was kept on ice) and the excess of the cross-linking reagent was removed by passing the hemoglobin solution through a Sephadex G-25 column (200 mm L×25 mm D) equilibrated with 50 mM borate pH 9.0. The resulting hemoglobin solution (3.6 g/dL) was again charged with CO. Poly(L-lysine) solutions were prepared in 50 mM borate pH 8.0 and added to hemoglobin (3.6 g/dL, 1.9 mL) as indicated in Table 1 below. The molar ratio of poly(L-lysine) to hemoglobin was 1:1 for all four polymers. The THb-poly (L-lysine) conjugates (THb-$K_n$) were sealed in serum bottles, recharged with CO and left at room temperature for two days. Hemoglobin concentrations in these samples were determined using Drabkin's reagent.

TABLE 1

| Poly(L-lysine) | Amount of poly(L-lysine) added to THb (mg) |
|---|---|
| $K_{4\ kDa}$ | 4.2 |
| $K_{7.5\ kDa}$ | 8.0 |
| $K_{26\ kDa}$ | 27.5 |
| $K_{37\ kDa}$ | 39.3 |

Anion Exchange Chromatography: Crude THb-$K_n$ complexes were analyzed using anion exchange chromatography on a SynChropak AX-300 column (250 mm L×4.6 mm D, SynChrom, Inc.). A sodium chloride gradient was used to elute various modified hemoglobins. The effluent was monitored at 280 nm.

By the time of analysis all unreacted THb-DBS had hydrolyzed to give THb. The reaction resulted in a mixture of products all of which, as expected, migrated before the THb on the anion exchange chromatography media. The yields were calculated by adding the peak areas of the early eluting peaks and comparing them to the total peak area. Yields of poly(L-lysine) modified hemoglobin calculated in this way were: 37, 37, 81 and 84% for $K_{4kDa}$, $K_{7.5kDa}$, $K_{26kDa}$ and $K_{37kDa}$, respectively.

Purification of THb-$K_n$ conjugates: THb-$K_n$ conjugates were separated from unconjugated THb by anion exchange chromatography on a POROS HQ/50 column (52 mm L, 14 mm D) equilibrated with 25 mM Tris-HCl buffer pH 8.4. Modified Hbs were eluted with a sodium chloride gradient. The effluent was monitored at 280 nm and pooled fractions containing THb-$K_n$ conjugates were concentrated using an Amicon™ diafiltration device and a 30 kDa cutoff membrane.

Size Exclusion Chromatography: The molecular weight distribution of purified THb-$K_n$ conjugates and their haptoglobin complexes was determined using size exclusion chromatography (SEC) on a Superdex™-200 column (300 mm L×10 mm D, Pharmacia) equilibrated and eluted with 0.5 M magnesium chloride containing 25 mM Tris-HCl pH 7.2 at a flow rate of 0.4 mL/min. The effluent was monitored at 280 nm and 414 nm. Hemoglobin to poly(L-lysine) stoichiometry ranged from 1:1, using 4 kDa poly(L-lysine), to heterogeneous constructs with stoichiometries up to 4:1 using the higher molecular weight poly(L-lysine) linkers, according to corresponding elution times with molecular weight standards. No unmodified THb was present. These constructs were stable under the high salt conditions of chromatography.

Example 2
Complex Formation Between THb-$K_n$ and Haptoglobin 1-1

The following stock solutions were used for the preparation of the complexes: 1.74 mg/mL haptoglobin 1-1 (Hp) in water and 1.0 mg/mL solutions of the THb-$K_n$ (all THb-$K_n$ concentrations represent hemoglobin concentrations) in 50 mM sodium borate pH 9.0. Haptoglobin (14 uL) was added to THb-$K_n$ in potassium phosphate pH 7.0 to give the following final concentrations: 0.12 mg/mL (1.22 uM) haptoglobin and 0.19 mg/mL (2.9 pM) THb-$K_n$ in 25 mM potassium phosphate pH 7.0 (200 pL final volume). After incubation for 180 min. at room temperature, the samples were analyzed using SEC.

Figure 2A:
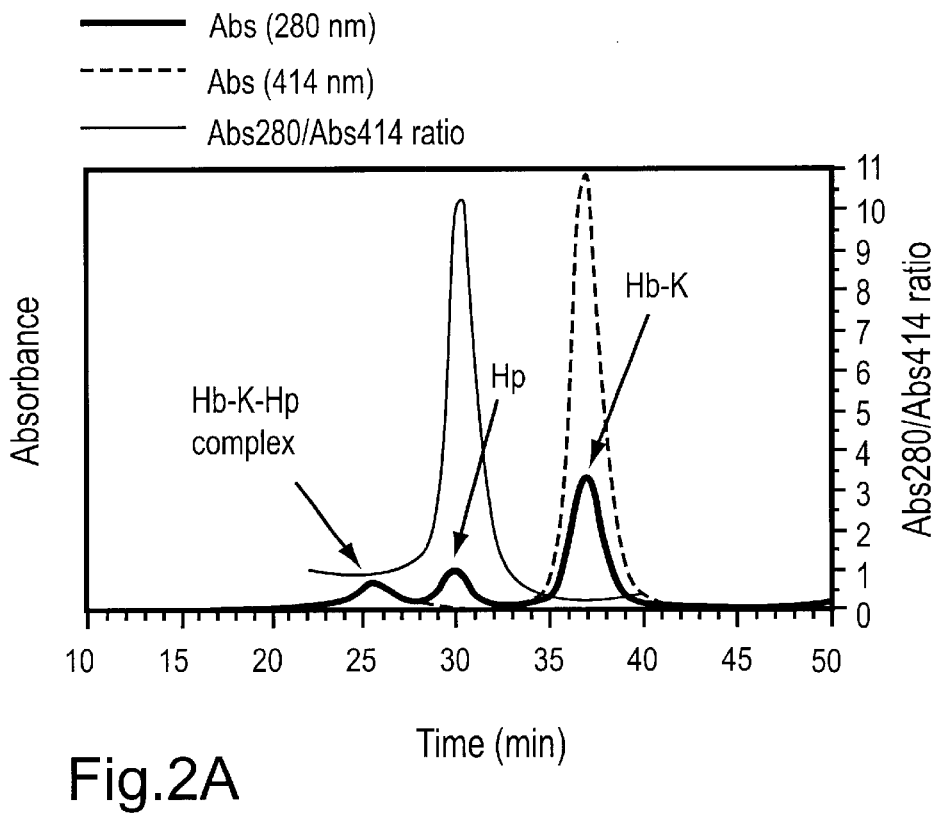
Figure 2B:
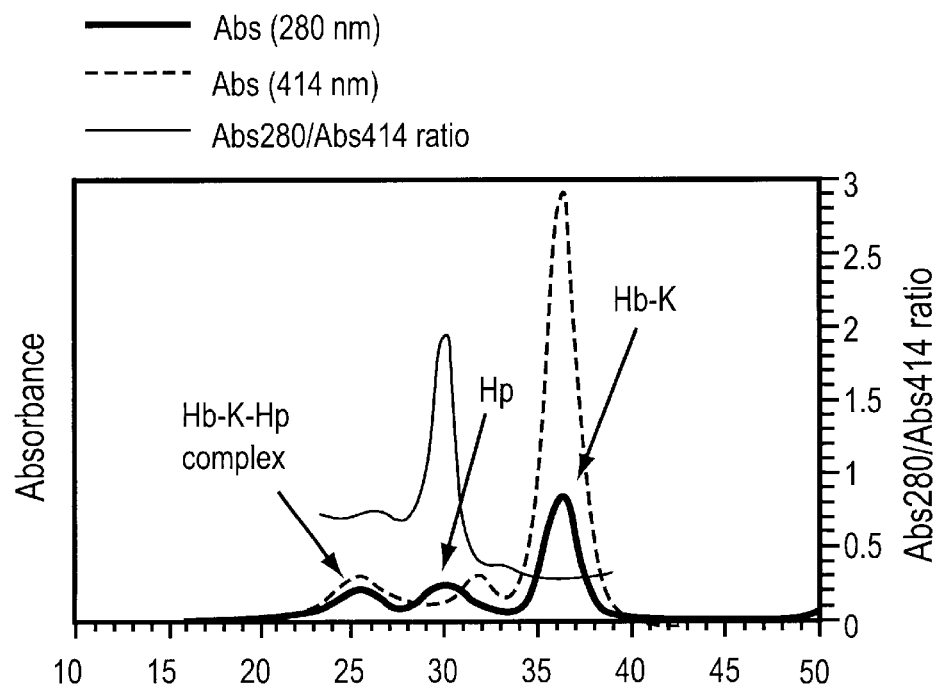
Figure 2C:
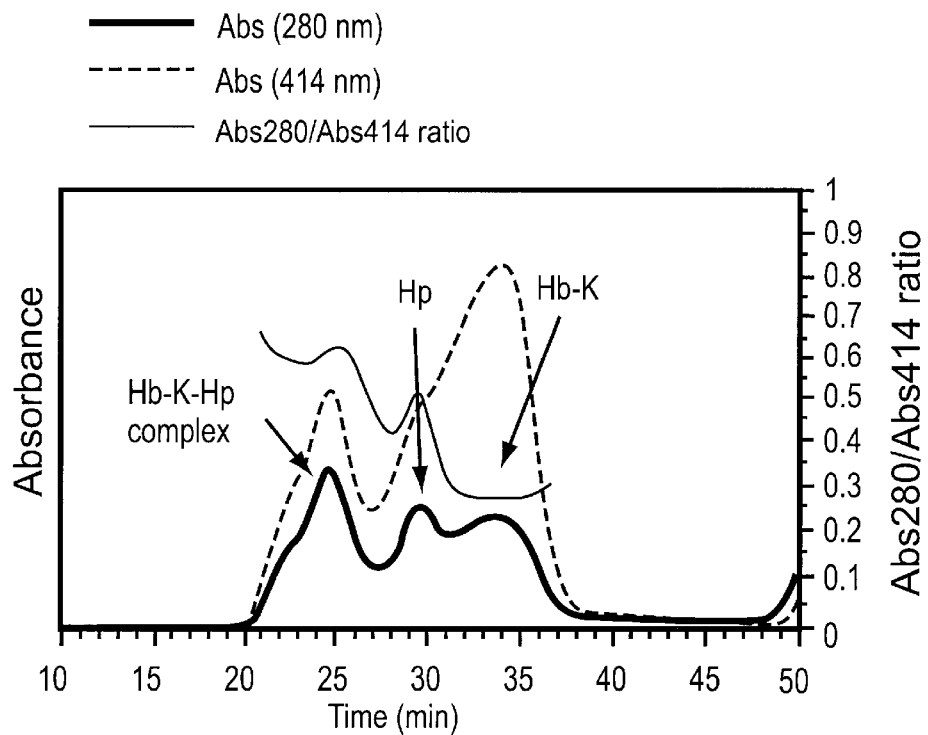
Figure 2D:
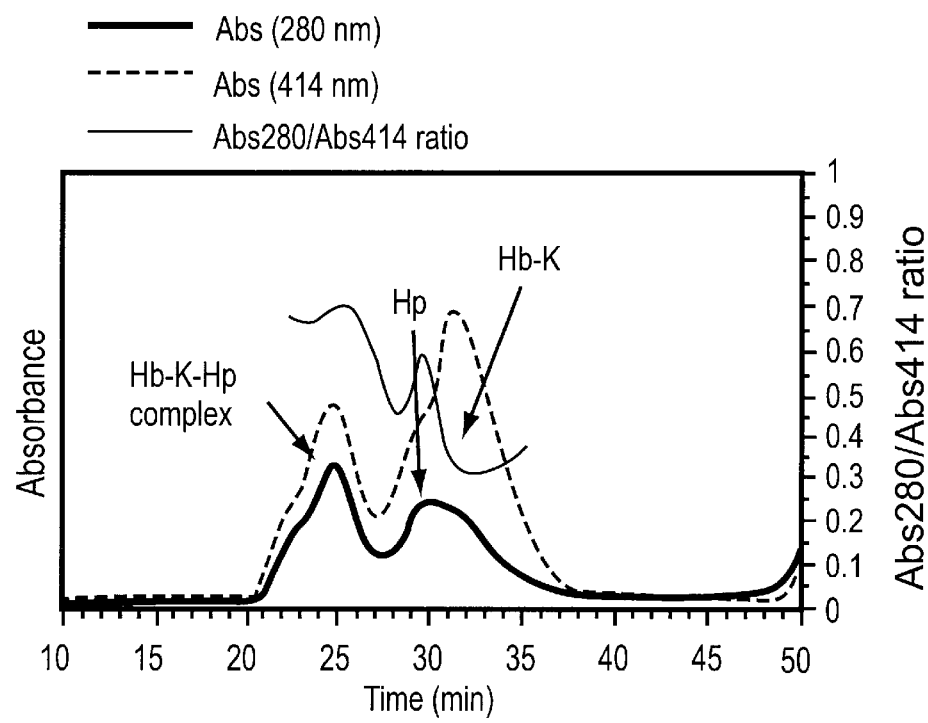

THb-$K_n$ complexes with haptoglobin 1-1: The formation of THb-$K_n$ complexes with haptoglobin can be followed using size exclusion chromatography (SEC). FIG. 2A shows the composition of the THb-$K_{4kDa}$ mixture with Hp after incubation at room temperature for 180 min. A new, high molecular weight peak appears at 25.5 min. Plots of the ratio of absorbance at 280 and 414 nm ($A_{280}/A_{414}$) over the elution period indicate the relative proportions of haptoglobin and hemoglobin in the construct-complexes and other peaks. The absorbance ratio ($A_{280}/A_{414}$) throughout the new peak is 0.9 indicating that both haptoglobin and hemoglobin components are present in this complex. Haptoglobin 1-1 migrates at 29.7 min. and is easily identified by high $A_{280}/A_{414}$ ratio. FIG. 2B shows SEC of the THb-$K_{7.5kDa}$ mixture with Hp after incubation at room temperature for 180 min. Again, a new peak appears at 25.1 min. with a $A_{280}/A_{414}$ ratio of 0.73, followed by haptoglobin at 29.7 min. and THb-$K_{7.5kDa}$ at 35.8 min. with $A_{280}/A_{414}$ ratio of 0.3. The analysis of the SEC of THb-$K_{26kD}$ and THb-$K_{37kDa}$ complexes with haptoglobin is more complicated due to their broad molecular weight distribution. The results are presented in FIGS. 2D and 2D respectively. It is evident from FIGS. 2C and 2D that both THb-$K_{26kDa}$ and THb-$K_{37kDa}$ form complexes with haptoglobin. The $A_{280}/A_{414}$ ratio is 0.64 for THb-$K_{26kDa}$-Hp and 0.69 for THb-$K_{37kDa}$-Hp.

Figure 3:
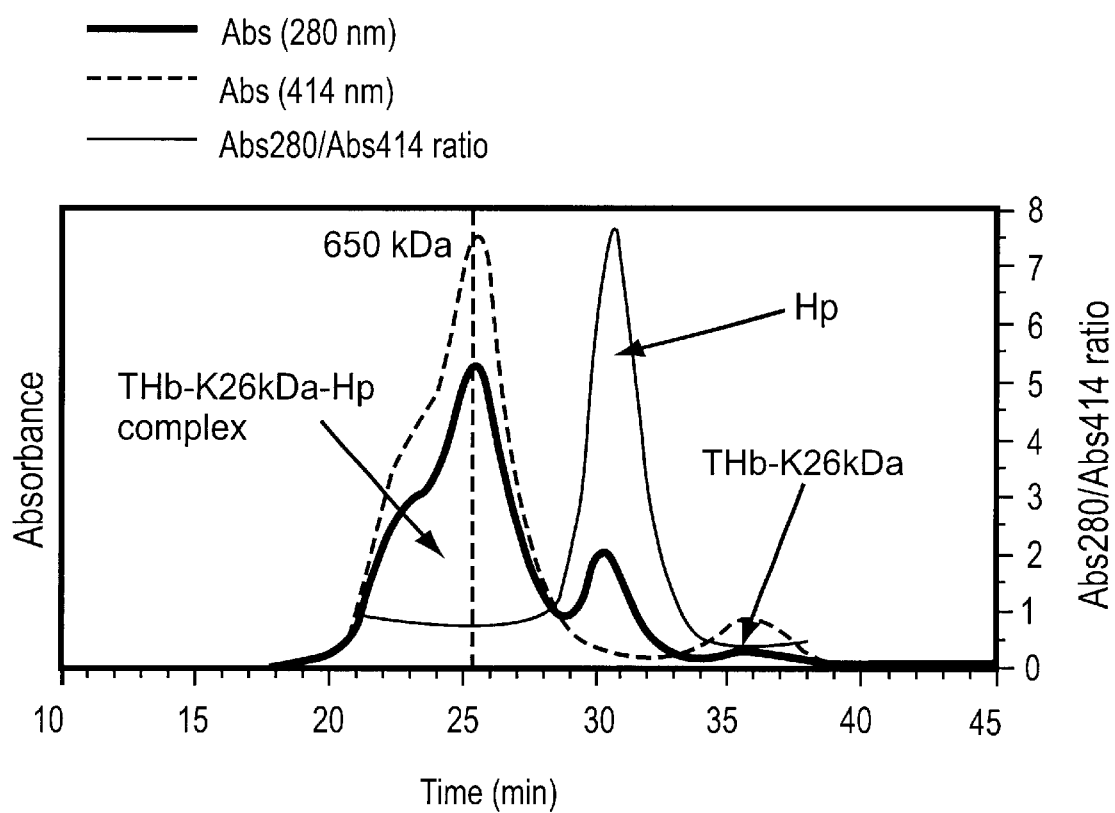
FIG. 3 is a similar plot, for the product complex utilizing 26 kDa poly(L-lysine) after 24 hours incubation with haptoglobin, produced in Example 2.

Degree of THb-$K_{26kDa}$-Hp complex formation: To determine whether all structurally different components of the THb-$K_n$ bind to haptoglobin, THb-$K_{26kDa}$ was incubated with a 15% excess of haptoglobin for various lengths of time and then analyzed using SEC. The following stock solutions were used for the preparation of the complex: 1.74 mg/mL haptoglobin 1-1 in water and 7.4 mg/mL solutions of THb-$K_{26kDa}$ in potassium phosphate pH 7.0 to give the following final concentrations: 0.74 mg/mL (7.5 mM) haptoglobin and 0.41 mg/mL (6.4 mM) THb-$K_{26kDa}$ (1.2:1 molar ratio of Hp to Hb) in 25 mM potassium phosphate pH 7.0. After incubation at room temperature for various lengths of time, the mixtures were analyzed using SEC. The progress of the reaction was followed by monitoring the disappearance of haptoglobin peak on a SEC profile. 85% of the THb-$K_{26kDa}$ was bound by haptoglobin after 24 hours. The resulting THb-$K_{26kDa}$-Hp complex has a broad molecular weight distribution ranging from 370 kDa to app. 1000 kDa (FIG. 3).

Example 3
DNA Binding to THb-$K_n$ and THb-$K_n$-Hp. Gel Mobility Shift Assay

Gel mobility shift assays were conducted to evaluate the stoichiometry of binding of plasmid DNA (pCMVbeta) to the THb-$K_n$ conjugates. This gel electrophoretic method is based on the observation that the migratory properties of the DNA are altered upon binding protein. Neither proteins nor DNA-protein complexes in which protein constitutes a significant part of their mass enter 1% agarose gels. If mixtures with an increasing THb-$K_n$ to DNA ratio are analyzed, it is observed that the DNA band disappears at and above the ratio that corresponds to the stoichiometry of the complex. For each of the four conjugates and for the THb-$K_{26kDa}$-Hp complex, solutions containing from 0.4 to 6400 ng of the conjugate (this weight based on the hemoglobin component) in 32 µL of 20 mM HEPES pH 7.3 containing 150 mM NaCl were prepared. The plasmid DNA (560 ng in 28 µL of 20 mM HEPES pH 7.3 containing 150 mM NaCl) was added dropwise to each sample and the mixtures were incubated for 1 hour at room temperature. The samples (15 µL) were analyzed on a 1% agarose gel containing ethidium bromide (0.2 µg/mL). The amount of conjugate which prevented DNA entry into the gel was determined. Results are described in the following Example.

Example 4
DNA Binding to THb-$K_{26kDa}$ and THb-$K_{26kDa}$-Hp Complex: Thiazole Orange Fluorescence Quenching Method This dye fluorescence assay is based on the observation that a DNA intercalating dye (thiazole orange) is fluorescent only if bound to DNA. Complex formation between THb-$K_n$ and DNA causes the displacement of the intercalating dye from DNA and the decrease of total fluorescence.

The following stock solutions were used in this experiment: 0.05 mg/mL DNA (pCMVbeta), 0.010 mg/mL, THb-$K_{26kDa}$ or THb-$K_{26kDa}$-Hp complex, 1.75×10$^{-6}$ M thiazole orange (0.1 mg/mL solution in 1% methanol was diluted 190 times with water), 20 mM HEPES pH 7.3 containing 0.15 M NaCl. Plasmid DNA (10 µL), THb-$K_{26kDa}$ (volumes varying from 2.5 to 60 µL) and buffer (to the final volume of 200 µL) were mixed in a generic 96 well plate and incubated for 2.5 hours at room temperature. Sample containing thiazole orange in HEPES buffer was also prepared and used as a background control. Fluorescence was measured on a Packard FluoreCount™ plate reader using excitation at 485 nm and emission at 530 nm. The THb-$K_{26kDa}$-Hp complex was prepared as described above and used without purification. It was diluted with 20 mM HEPES pH 7.3 containing 0.15 M NaCl to give a final concentration of 0.010 mg Hb/mL.

Figure 4A:
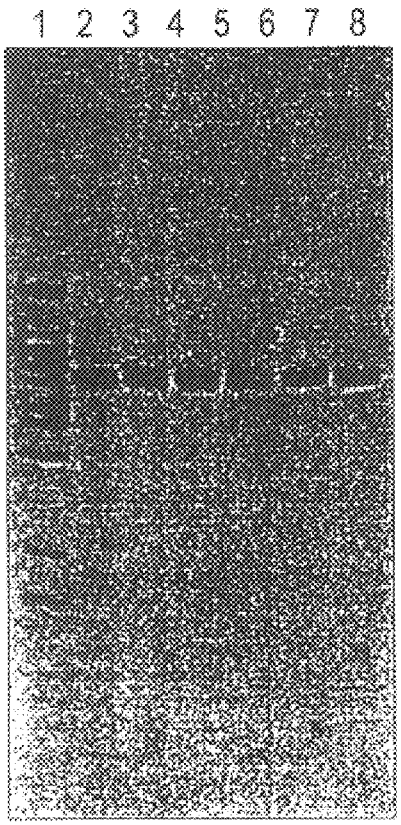
FIG. 4 represents are depictions of gel mobility shift assays of DNA in the presence of (A) THb and (B) THb-poly(L-lysine) produced according to Example 4.
Figure 4B:
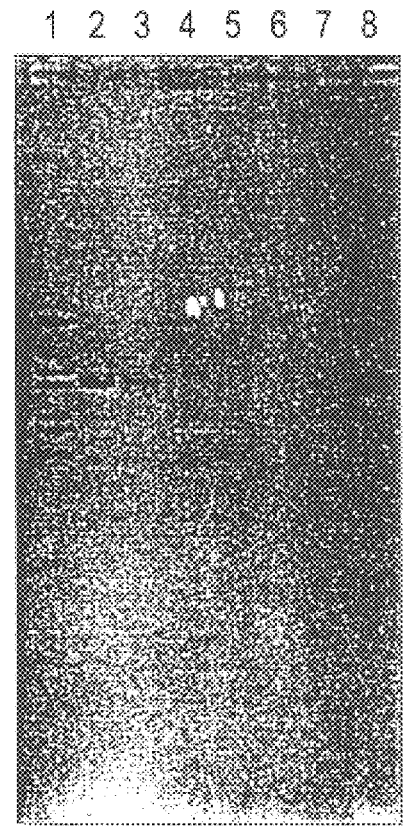
Figure 5:
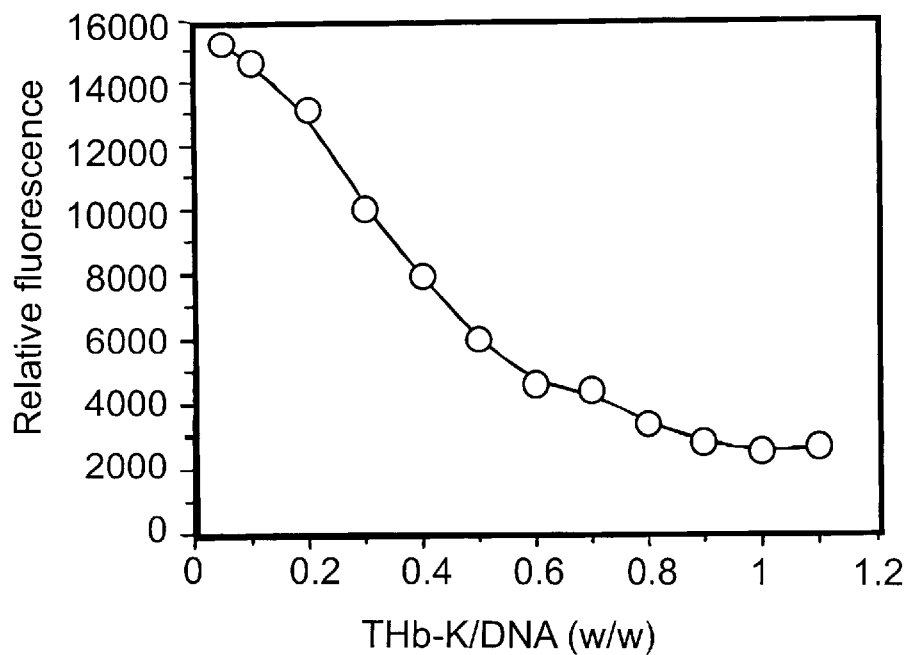
FIG. 5 is a dye fluorescence assay of the products of Example 4.

The gel mobility shift assay and the fluorescence quench assay both demonstrated that THb-$K_n$ binds to DNA. FIG. 4A (left) and 4B (right) are depictions of gel mobility shift assays of haptoglobin-hemoglobin-DNA conjugates produced according to Example 4. One hundred and forty ng of DNA were added to increasing amounts of (A) THb or (B) THb-$K_{26kDa}$. Lane 1 of both gels contain DNA molecular weight markers. Hb content in other lanes: (A2) 50 ng, (A3) 100 ng, (A$) 200 ng, (A5) 400 ng, (A6) 800 ng, (A7) 1600 ng, (A8) empty, (B2) 25 ng, (B3) 50 ng, (B4) 100 ng, (B5) 200 ng, (B6) 400 ng, (B7) 800 ng, (B8) DNA only. As regards the gel mobility shift assay, increasing the proportion of THb-$K_n$ in the DNA samples affected DNA migration as seen in FIG. 4. FIG. 4A shows the migratory properties of DNA after incubation with increasing amount of THb ranging from 50 to 1600 ng of protein. In this concentration range THb does not bind DNA, since no change in DNA migration can be detected. THb-$K_{26kDa}$ is most effective at binding DNA. One hundred ng of THb-$K_{26kDa}$ (THb-$K_{26kDa}$ to DNA ratio=0.7, w/w) completely prevents the DNA from entering the agarose gel (FIG. 4B). Approximately 400 ng of the other THb-$K_n$ preparations were required to bind all DNA. The results for THb-$K_{26kDa}$ are in good agreement with the fluorescence quench assay which indicated 86% of fluorescence decrease at the same THb-$K_{26kDa}$ to DNA ratio. FIG. 5 shows the effect of $THb_{26}kDa$ on DNA-thiazole orange fluorescence. On FIG. 5, the amount of THb-$K_{26kDa}$ is based on the hemoglobin component only.

Figure 7:
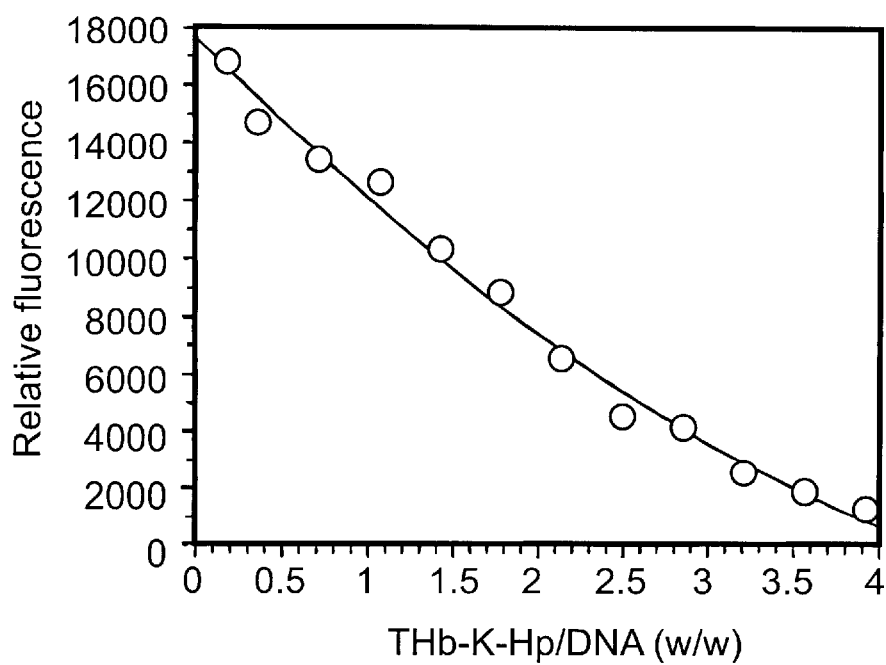
FIG. 7 is a fluorescence assay of another product of Example 4.
Figure 6:
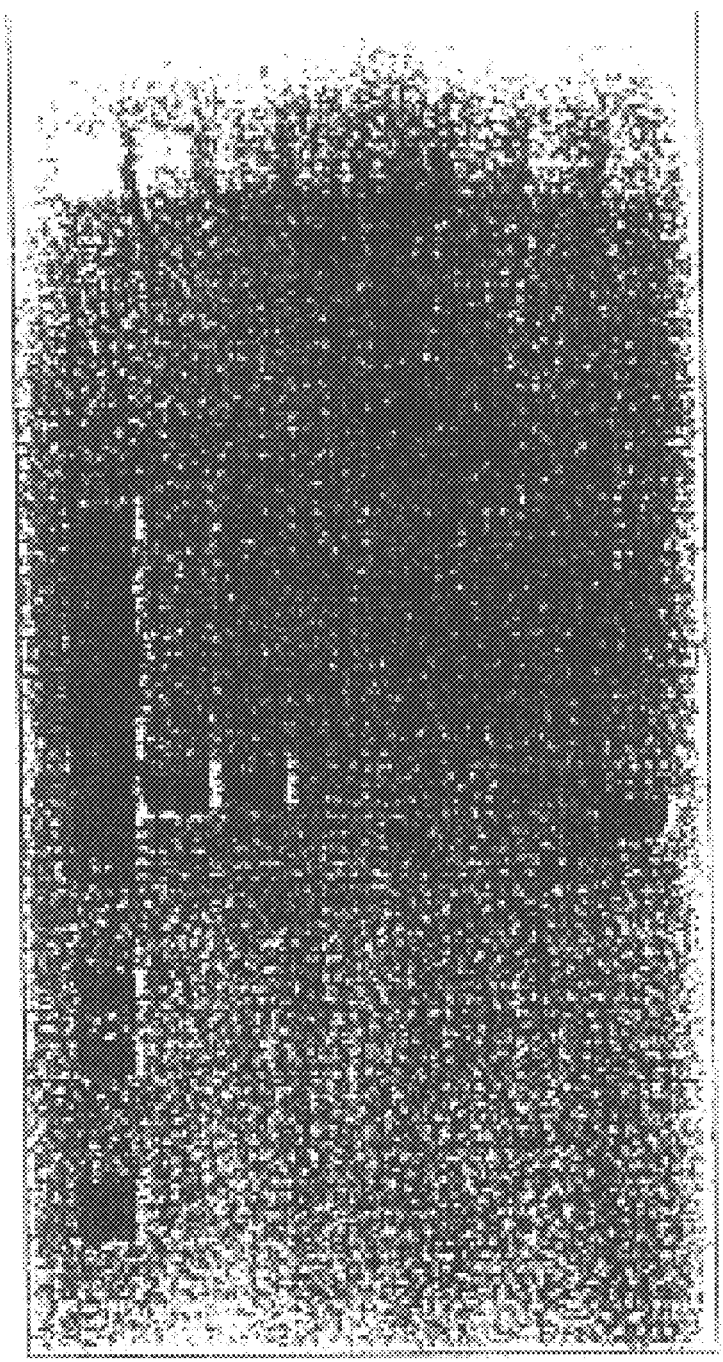
FIG. 6 is a depiction of the gel mobility shift assay of the products of Example 4.

The THb-$K_{26kDa}$-Hp complex also binds DNA. It was found that 200 ng of THb-$K_{26kDa}$-Hp completely prevented 140 ng of DNA from entering the agarose gel (THb-$K_{26kDa}$-Hp to DNA ratio=1.4, w/w) . FIG. 6 shows THb-$K_{26kDa}$-Hp binding to DNA by gel mobility shift assay. One hundred and forty ng of DNA were added to increasing amounts of THb-$K_{26kDa}$-Hp: 25 ng (lane 2), 50 ng (3), 100 ng (4), 200 ng (5), 400 ng (6), 800 ng (7), weights based on the hemoglobin component. Molecular weight standards were loaded in lane 1 and 140 ng of DNA in lane 8. At the same THb-$K_{26kDa}$-Hp to DNA ratio (1.4:1 w/w) the fluorescence assay indicates only 42% of fluorescence decrease and 81% fluorescence decrease at 2.8 ratio. The fluorescence assay is shown in FIG. 7 (the weight of the conjugate is based on the hemoglobin component thereof only). Comparison of the gel mobility shift assays for THb-$K_{26kDa}$-Hp indicates that approximately twice as much protein-bound poly(L-lysine) is required to prevent DNA from migrating into the gel when the haptoglobin complex is used. Since the amount of hemoglobin conjugated poly(L-lysine) was identical in both experiments, the decreased DNA binding ability of THb-$K_{26kDa}$-Hp is probably due to steric crowding in the THb-$K_{26kDa}$-Hp-DNA complex.

In these examples, there has been synthesized and characterized a construct having all the necessary components for in vivo targeted gene delivery to human hepatocytes through haptoglobin receptors. Poly(L-lysine) was conjugated to the TTDS cross-linked hemoglobin to provide a site for binding DNA through electrostatic interactions of its positively charged ε-amine groups with the negative charges of phosphate groups on DNA. It has been previously demonstrated that when more than 90% of DNA's negative charges are neutralized, the linear DNA strand is compacted into a toroid structure, a form which is more stable and more amenable to internalization by cells. Optimal gene expression has been reported for the DNA to poly(L-lysine) ratios which result in electroneutral complexes.

The gel mobility shift and the fluorescence assays have demonstrated that THb-$K_{26kDa}$-Hp complex binds the plasmid DNA thus completing the assembly of a construct potentially capable of delivering oligonucleotides by haptoglobin receptor-mediated endocytosis.

Example 5
Synthesis of Crosslinked Hemoglobin Bearing Tritiated or Non-tritiated Lysine A solution of L-[$^3$H]-lysine was evaporated under a stream of nitrogen to obtain 59.5 nmole (5 mCi) of solid material. 59.5 nmole of non-radiolabeled L-lysine was prepared in a similar manner. TTDS (39.8 mg) was dissolved in ethanol (270 μmL) and 200 μL of this solution was added to deoxyhemoglobin (10 mL, 9.2 g/dL) in 50 mM borate pH 9.0. The reaction mixture was stirred at room temperature under nitrogen for one hour, then oxygenated. Excess crosslinker was removed from half of the mixture by gel filtration and then the solution was CO charged and frozen, giving crosslinked Hb with an activated ester on the crosslinker (THb-DBS, 62 mg/mL) as described by Kluger (U.S. Pat. No. 5,399,671). Unreacted crosslinker was removed from the other half of the crude reaction mixture by gel filtration using 0.1 M L-lysine/L-lysine hydrochloride elution buffer (pH 9.0). The eluate was CO charged and left at room temperature overnight. Using this process, lysine became conjugated to the linker via the activated ester, giving THb-Lys. Freshly thawed THb-DBS (29.5 nmole, 30.5 μL) was added to the radiolabeled and the non-radiolabeled lysines each day for three days. THb-Lys (700 pL) was then added to both mixtures and the products desalted. Completion of the reaction was confirmed by anion exchange chromatography.

Example 6
Haptoglobin-THb-Lys Complex

Figure 8:
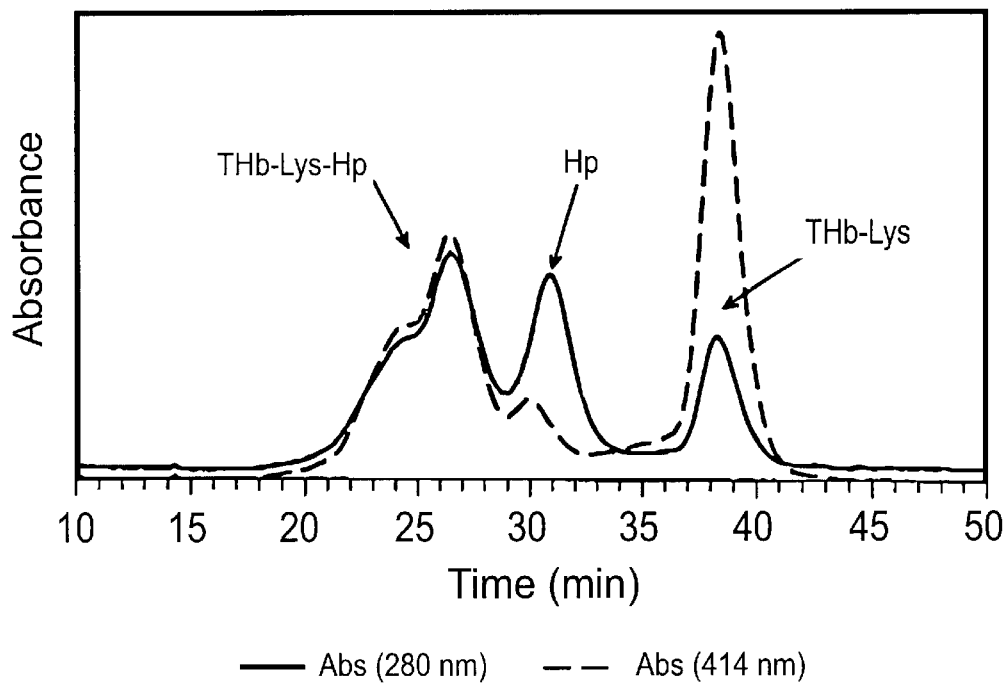
FIG. 8 is a size exclusion chromatogram of the product of Example 6.

Haptoglobin (1.61 mg/mL haptoglobin 1-1 in water, 11 μL) was added to THb-Lys (38 mg/mL in 50 mM sodium borate pH 9.0) to give the following final concentrations: 0.68 mg/mL (6.9 μM) haptoglobin and 0.41 mg/mL (6.4 μM) THb-Lys were made up to a final 200 μL volume at 25 mM potassium phosphate pH 7.0. Within 18 hours, the haptoglobin-THb-Lys complex was observed by SEC as a high molecular weight species, with absorption at 280 and 414 nm, eluting separately from native haptoglobin and the original THb-Lys product (FIG. 8). The construct-complex was purified by SEC. The column was equilibrated and eluted with phosphate-buffered saline (PBS).

Example 7
Haptoglobin-THb-[$^3$H]-Lys Complex

THb-[$^3$H]-Lys (75 μL, 41 mg/mL, 0.657 Ci/mmole) was added to a solution of partially purified haptoglobin 1-1 (0.273 mL, 3.7 mg/mL) in PBS pH 7.4. The mixture was incubated at room temperature overnight. The THb-[$^3$H]-Lys-Hp complex was purified using SEC equilibrated and eluted with PBS pH 7.4. Radioactivity was associated primarily with a high molecular weight species identified by SEC, having absorption at 280 and 414 nm and eluting separately from native haptoglobin and the original THb-Lys product, and with a retention time corresponding to the non-radiolabeled product of Example 6.

Example 8
Synthesis of Fluorescein-hemoglobin Conjugate (FL-Hb)

5-Iodoacetamido fluorescein (5-IAF, 11 mg, 21 μmol) solution in N,N-dimethylformamide (DMF, 50 μL) was slowly added to oxyhemoglobin (60 mg/mL, 5 mL) in 50 mM potassium phosphate pH 7.0 with stirring at 4° C. After three hours of reaction at 4° C., the excess of 5-IAF was removed by extensive dialysis against 50 mM potassium phosphate pH 7.2 until no 5-IAF could be detected in the dialysate. The UV-visible absortion spectrum of the product showed a characteristic fluorescein absorption band at 496 nm.

Figure 9A:
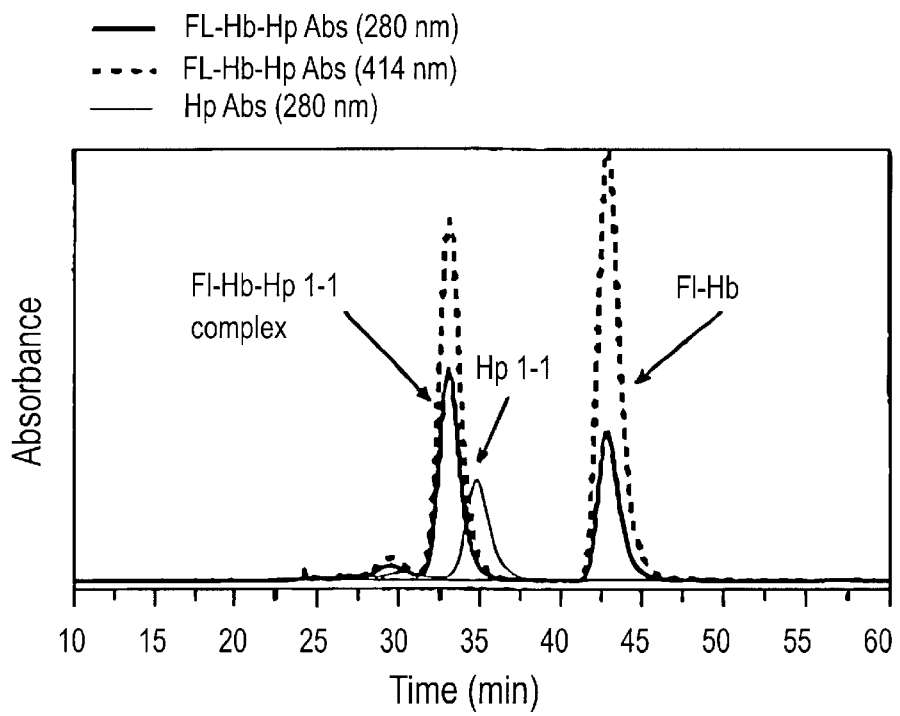
Figure 9B:
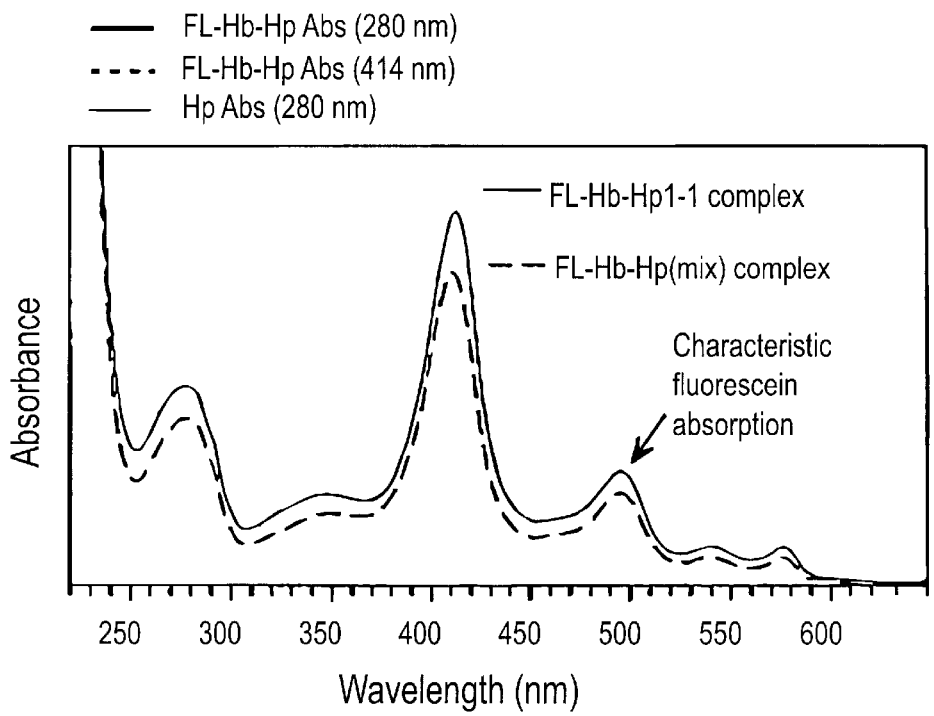
Figure 9C:
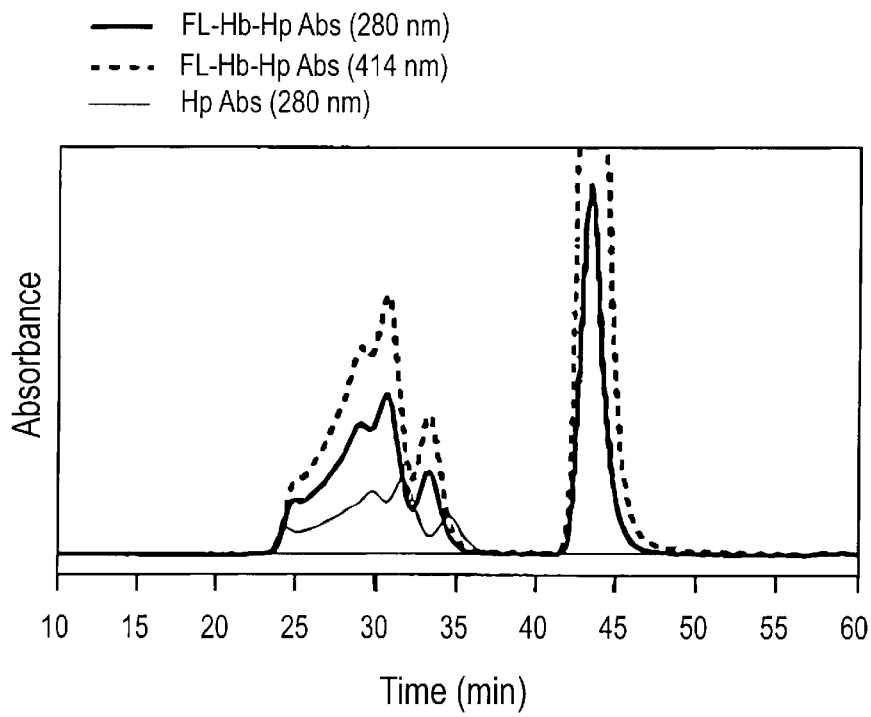
Figure 9D:
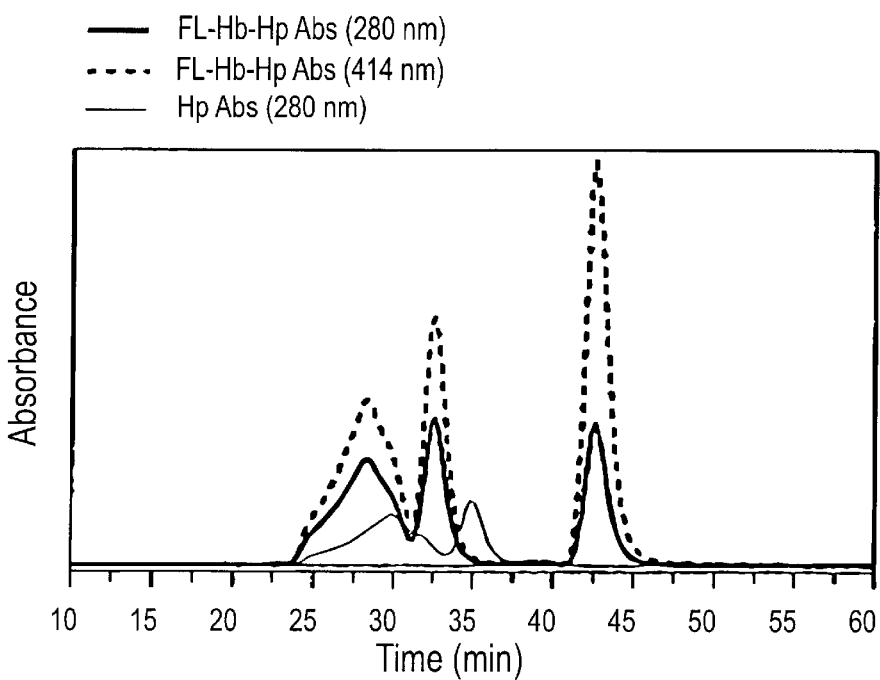

Example 9
Complexes of FL-Hb with Haptoglobin 1-1, 2-1 and Mixed Phenotype Haptoglobin FL-Hb (6 mg/mL in 50 mM potassium phosphate pH 7.2, 40 μL) was added to haptoglobin 1-1, 2-1 or mixed phenotype ($Hp_{mix}$) (2.8 mg/mL in water, 39 μL) to give the following final concentrations: 0.6 mg/mL (6.2 μM) Hp and 1.3 mg/mL (21 gM) FL-Hb in 180 μL final volume of 25 mM potassium phosphate pH 7.0. The mixture was analyzed by SEC after incubation at room temperature for 10 min. FL-Hb complex with haptoglobin 1-1 migrates at 33 min.(FIG. 9A—overlaid SEC chromatograms of Hp 1-1 and Hp 1-1 complex with Fl-Hb) and can be clearly distinguished from haptoglobin by its absorbance at 414 nm. FL-Hb migrates at 42.9 min. (FIG. 9A). FL-Hb complexes with Hp 1-1 and Hpmix were isolated and analyzed by UV-Vis spectroscopy (FIG. 9B—UV-Vis spectrum of haptoglobin 1-1 and $Hp_{mix}$ complexes with FL-Hb, the arrow indicates the band characteristic of fluorescein) and fluorimetry. This material shows fluorescence with excitation at 480 nm and emission at 520 nm, and a characteristic absorption band for fluorescein with $\lambda_{max}$ at 496 nm. FL-Hb complexes with Hp 2-1 and $Hp_{mix}$ are shown in FIGS. 9C and 9D, respectively. The construct-complexes were purified by SEC eluted with PBS buffer.

Example 10
Synthesis of Cross-linked Hemoglobin Bearing Tritiated Putrescine 200 mL of purified Hb was diafiltered into 50 mM borate buffer pH 9.0, then deoxygenated and the concentration adjusted to 7.1 g/dL. Hb was crosslinked at a 2:1 ratio of TTDS to Hb for 45 min at 30° C. and then desalted using 50 mM borate pH 9.0 buffer yielding a final concentration of 3.1 g/dL. 1.43 mL of the desalted Hb was added to each of two 1 mL aliquots of radiolabeled putrescine (1 mCi/mL, $6.94 \times 10^{-5}$ mmol/mL) and reacted at room temperature for 1.5 hours (10:1 Hb:putrescine ratio). 0.9 mg of cold putrescine (40 fold excess over radiolabeled putrescine) was reacted with 17 mL of the THb-DBS at a ratio of 1.5:1 THb-DBS:putrescine. 5 mL of this solution was added to each of the two reactions and mixed overnight at room temperature. Both mixtures were then added to freshly crosslinked and desalted THb-DBS ($5.3 \times 10^{-5}$ moles) and reacted at room temperature for 1.5 hours. A 20 fold excess of cold putrescine (172 mg) was then added and reacted overnight. The THb-[$^3$H]Pu was then diafiltered into Ringers Lactate. The specific activity was 1.5 Ci/mole, 90 mg/mL.

Example 11
Haptoglobin 1-1 Complex with THb-[$^3$H]Pu

Haptoglobin (3.0 mg/mL in water, 51 μL) was added to THb-[$^3$H]Pu (10 mg/mL in PBS pH 7.2, 20 μL) to give the following final concentrations: 1.4 mg/mL (14 μM) haptoglobin and 1.8 mg/mL (28 μM) THb-[$^3$H]Pu in a final 110 μL volume of 25 mM potassium phosphate pH 7.0. The mixture was analyzed by SEC after incubation at room temperature for 2 hours. Fractions (0.4 mL) of the effluent were collected and analyzed by scintillation counting. THb-[$^3$H]Pu-Hp complex migrates as a high molecular weight species with elution time from 20 to 28 min. (FIG. 10) and is well separated from haptoglobin band at 30 min. and THb-[$^3$H]Pu at 37 min. THb-[$^3$H]Pu -Hp absorbs both at 280 nm and 414 nm ($A_{280nm}/A_{414nm}=0.74$) and has specific radioactivity (cpm/mg Hb) similar to that of THb-[$^3$H]Pu. The construct-complex was purified by SEC.

Example 12
Synthesis of Cross-linked Hemoglobin Bearing Monodansyl Cadaverine Purified Hb (8.0 g/dL, 100 mL, $1.25 \times 10^{-4}$ moles) was diafiltered into 50 mM borate buffer, pH 9.0, then oxygenated and deoxygenated. A deoxygenated solution of TTDS (2 fold molar excess over Hb, 0.26 g, $2.5 \times 10^{-4}$ moles) was added and the mixture was stirred for 1 hour at 35° C., then charged with CO. Ion exchange chromatography at this time indicated only a small amount of unreacted Hb (1.7%). A 15-fold molar excess of monodansylcadaverine (MDC) in ~20 mL of 0.1 M HCl adjusted to 25 mL with 50 mM borate, pH 9.0 was added to the crosslinked Hb (0.63 g, $1.88 \times 10^{-3}$ moles). After 60 hours at room temperature, the MDC-Hb was diafiltered against 10 mM borate, pH 9.0. The product was purified by gel filtration and diafiltered into Ringers Lactate.

Example 13
Haptoglobin 1-1 Complex with THb-MDC

THb-MDC (20 mg/mL in Lactated Ringer's solution pH 7.2, 3.5 μL) was added to haptoglobin 1-1 (1.1 mg/mL in water, 200 μL) to give the following final concentrations: 1.1 mg/mL (11 μM) Hp and 0.34 mg/mL (5.4 μM) THb-MDC. The mixture was analyzed by SEC after incubation at room temperature for 24 hours. THb-MDC complex with haptoglobin migrates as a high molecular weight species with elution time from 21 to 29 min (FIG. 11). This material migrates separately from haptoglobin (30.9 min.) and absorbs at both 280 nm and 414 nm ($A_{280nm}/A_{414nm}=0.70$). THb-MDC elutes at 37.9 min. with $A_{280nm}/A_{414nm}=0.29$. The construct-complex can be purified by SEC.

Example 14
Synthesis of Cross-linked Hemoglobin Bearing Primaquine (THb-PO)

TTDS (14.0 mg) in ethanol (100 μL) was added to deoxyhemoglobin (10 mL, 58 mg/mL) in 50 mM borate pH 9.0. The reaction mixture was stirred at room temperature under nitrogen for one hour. The excess of the cross-linker was then removed by gel filtration eluted with 50 mM borate pH 9.0 and the product (THb-DBS, 43 mg/mL) was charged with CO. Primaquine diphosphate (0.5 g, 1.1 mmol) was dissolved in 50 mM borate pH 9.0 (10 mL) and the pH of the resulting solution was adjusted to 8.5 with 10 M NaOH (primaquine partially precipitated). THb-DBS (10 mL) was added to primaquine and the reaction mixture was stirred in the dark at room temperature overnight. The product was then filtered and the filtrate dialyzed extensively against 50 mM borate pH 9.0. Anion exchange chromatography of the product (FIG. 12) indicates that THb-PQ constitutes 68% of all hemoglobin components in the mixture. THb-DBS conjugated with primaquine constitutes 64% of all f chains when the product is analyzed using reversed phase chromatography.

Example 15
Haptoglobin 1-1 Complex with THb-PO

THb-PQ (15 mg/mL in 50 mM borate pH 9.0, 67 μL) was added to haptoglobin 1-1 (4.0 mg/mL in water, 500 μL) to give the following final concentrations: 2.0 mg/mL (20 μM) Hp and 1.0 mg/mL (15.7 μM) THb-PQ. The mixture was analyzed by SEC and anion exchange chromatography after incubation at room temperature for 21 hours. THb-PQ complex with haptoglobin migrates as a high molecular weight species with elution time from 21 to 29 min. (FIG. 13). This material migrates separately from haptoglobin complexed with uncross-linked hemoglobin (29.9 min.) and haptoglobin (30.6 min.) and absorbs at both 280 nm and 414 nm ($A_{280nm}/A_{414nm}=0.70$). Anion exchange chromatography indicated that all unmodified hemoglobin and 74% of both THb-PQ and THb have reacted with Hp. This result is in good agreement with the SEC analysis which indicates that 78% of hemoglobin has reacted with Hp.

Example 16
Haptoglobin-[poly-O-raffinose-Hb] and Haptoglobin-[64 kDa-O-raffinose-Hb] Complexes HbA0 was crosslinked and polymerized using oxidized raffinose (OR) according to the procedure of Pliura (U.S. Pat. No. 5,532,352). Molecular weight species greater than 64 kDa, representing polymerized Hb (>64 kDa OR-Hb), where separated from 64 kDa species (64 kDa OR-Hb) by size exclusion chromatography. Hb preparation were combined separately with human haptoglobin 1-1 in water to a final concentration of 0.2 mg Hb/mL and 0.125 mg haptoglobin/mL (final Hb:Hp approximately 2.2:1). The mixtures were incubated for one hour at 22° C., then analyzed by size exclusion chromatography under dissociating, non-denaturing elution conditions (0.5 M $MgCl_2$, 25 mM Tris pH 7.4). FIG. 14, which shows size exclusion chromatography elution profiles with detection at 280 (solid lines) and 414 nm (broken lines), indicates binding of the modified hemoglobins with haptoglobin. Incubation of the modified hemoglobins with haptoglobin results in high molecular weight species which do not correspond to either the modified hemoglobin or haptoglobin, and which have absorption at 414 nm indicating hemoglobin content.

Example 17
Binding of Modified Human Hb ([$^3$H]-NEM-Hb) to Rat Haptoglobin in Plasma 1 mCi of $^3$H-N-ethylmaleimide ([$^3$H]-NEM) in pentane was evaporated in 0.5 mL phosphate buffer, and 25 mg of Hb in 1 mL buffer was added giving a final NEM:Hb ratio of 0.06:1, or 37 μCi/mg Hb. RP HPLC analysis after 24 hours at 4° C. indicated incorporation of the majority of the radiolabel into a modified beta peak. After 47 hr, a 15-fold excess (over βCys93 thiol) of non-radiolabeled NEM was added. Salts and unbound NEM were removed by gel filtration, and the final concentration adjusted to 10.2 mg Hb/mL. A small portion of this material ($^3$H-NEM-Hb) was then combined with rat serum containing haptoglobin to determine if all radiolabeled components bound to Hp. The Hb-binding capacity of the rat serum was adjusted to 670 pg Hb/mL serum. 0.5 and 2.0 equivalents of $^3$H-NEM-Hb, based on Hb-binding capacity, were combined with serum and analyzed -by size exclusion chromatography eluted under dissociating, non-denaturing conditions using 0.5 M $MgCl_2$, 25 mM Tris pH 7.4 (FIG. 15). In the $^3$H-NEM-Hb preparation, all radioactivity was associated with a 32 kDa peak. At 0.5 eq. $^3$H-NEM-Hb, all radioactivity appeared in the Hb-haptoglobin peak (31 minutes). At 2.0 eq., haptoglobin is saturated and excess $^3$H-NEM-Hb remains unbound (41 minutes). 7.3% of the radioactivity combining with plasma components appears in a high MW peak at 22 minutes. These findings demonstrate that all components of the modified human Hb, $^3$H-NEM-Hb, are capable of binding rat haptoglobin in plasma.

Example 18
Biodistribution of Modified Hb and Haptoglobin Complexes in Rat

Figure 16A:
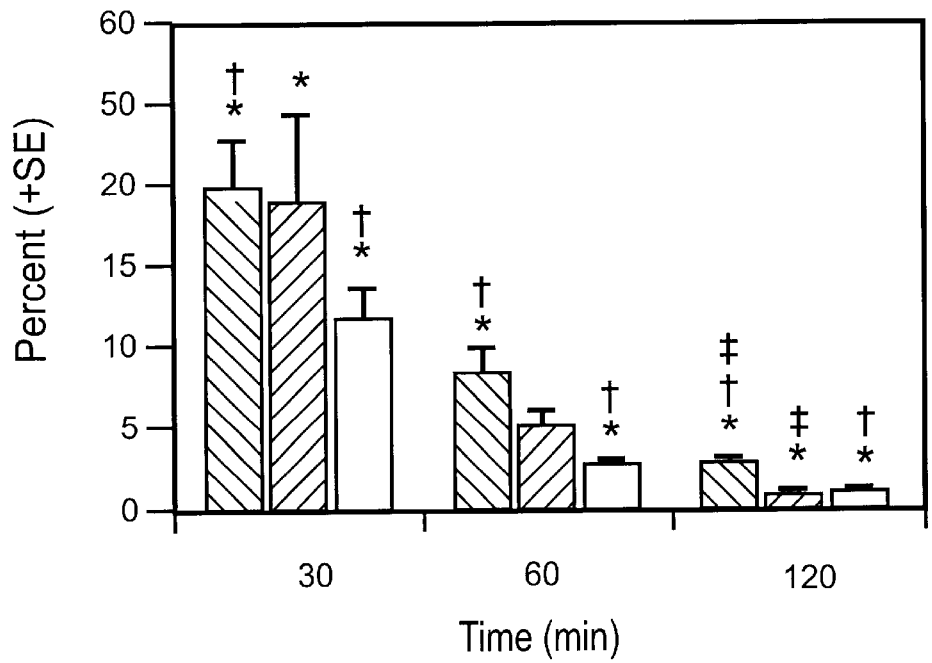
Figure 16B:
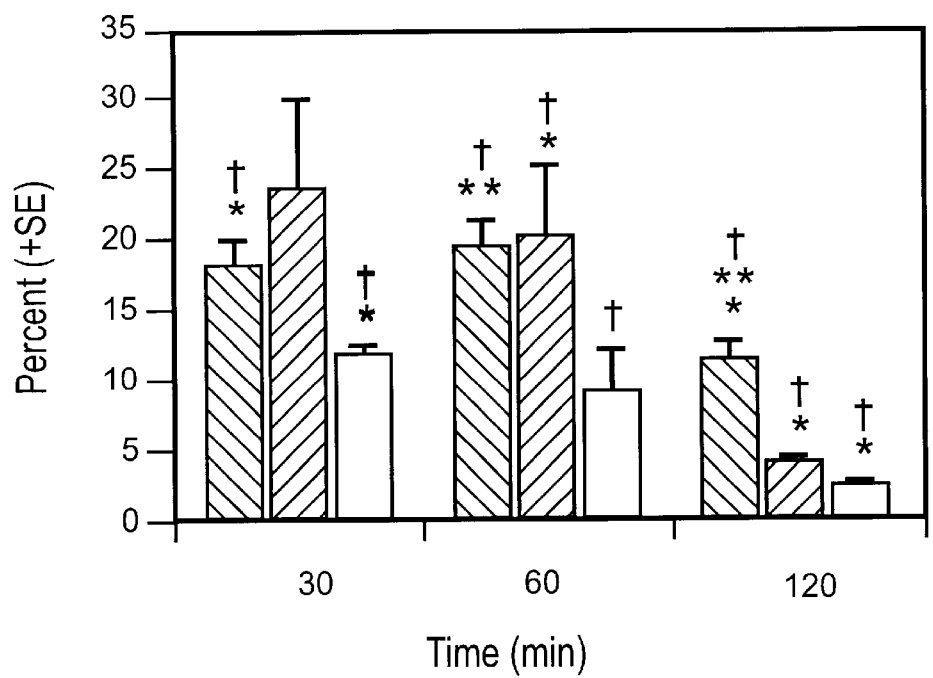
Figure 16C:
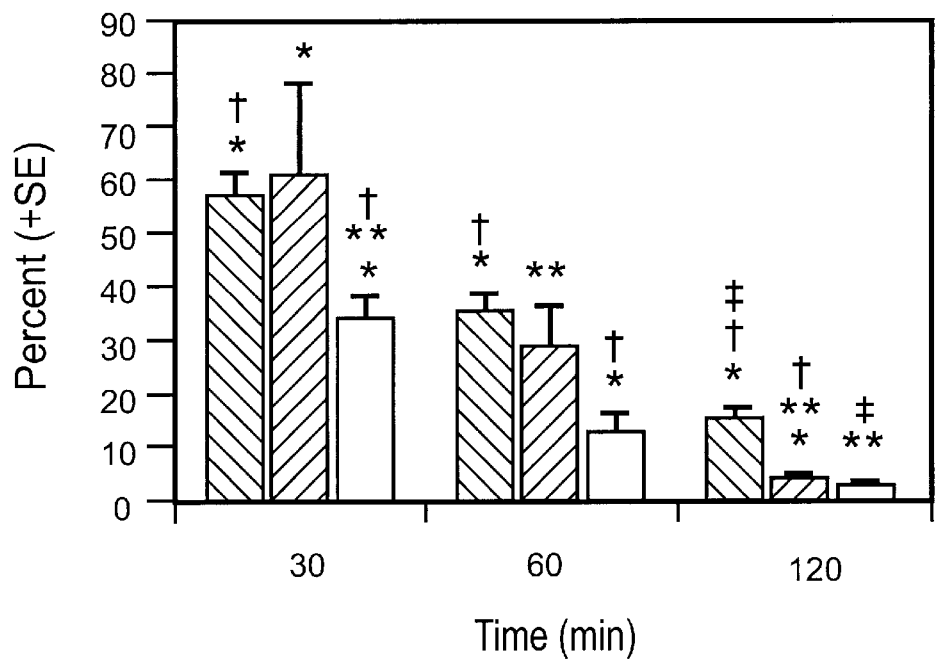
Figure 16D:
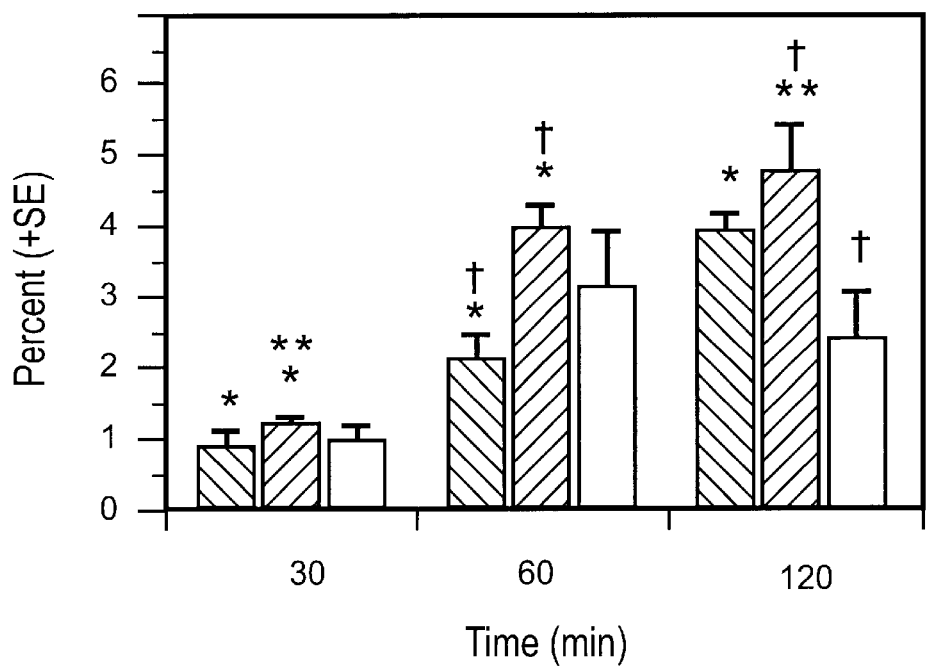

The ability of Hp to target modified Hb to the liver was measured in a radioisotope biodistribution study. Two test articles were prepared from purified human $HbA_0$ modified with tritium-labeled N-ethylmaleimide ([$^3$H]-NEM-Hb): [$^3$H]-NEM-Hb alone in Ringer's lactate, and [$^3$H]-NEM-Hb complexed to a slight excess of rat haptoglobin in rat plasma. Three treatment groups were analyzed; (A) normal rats received the modified Hb-haptoglobin complex in plasma, (B) normal rats received the modified Hb only (approximately twice the Hb-binding capacity of the rat), and (C) haptoglobin-depleted rats received the modified Hb only. Approximately 3 mg of Hb were administered to conscious Sprague-Dawley rats in each case. Liver and plasma samples were collected at 30, 60 and 120 minutes post-administration and radioactivity counted after solubilization and quenching. Values were converted to percentages of total dose and concentration/dose, and various analyses are shown in FIG. 16. This shows radioactivity contents, indicative of dose percentages. FIG. 16A shows the percentage of dose in plasma. FIG. 16B shows the percentage of dose in liver. FIG. 16C shows the percentage of dose in liver +plasma. FIG. 16D shows the liver/plasma concentrations. Star designations (* and **) show differences (p<0.05) within treatment groups at different times. Crosses (t and t) show differences (p<0.05) within time points for different treatment groups.

Plasma retention was highest in group A, and both groups A and B were higher than group C. The greatest difference in plasma content was at 120 minutes at which time group A plasma contained 3 times the radioactivity of group C and 3.5 times that of group B. Liver content in groups A and B was higher than in group C at all time points. At 30 minutes, groups A and B had approximately 20% of the total dose in the liver compared to 11% in group C. Liver content was the same at 30 and 60 minutes in groups A and B, and declined by the 120 minute time point. By 120 minutes, group A and B liver contents were 5- and 2-fold higher than group C, respectively. Groups A and B contained 60% of the dose in the plasma and liver compartments at 30 minutes, compared with roughly half that amount in the Group C animals. Liver to plasma concentration/dose ratios increased with time in all groups, with liver concentration approximately 4 times that of plasma in groups A and B by 120 minutes, roughly twice the ratio of group C at the same time. The improvement in plasma retention and liver targeting is further demonstrated by comparison of mean combined liver and plasma contents between groups, presented in FIG. 17, namely the ratios of mean combined liver and plasma percentages of total dose. Shaded bars are derived from Group A/C, solid bars from Group B/C, and open bars from group A/B. Group A and B combined liver and plasma contents were consistently greater than in group C, with group A having a combined content 4 times greater than in group C at 120 minutes. Areas under the distribution curves were calculated without extrapolation to time zero (Table 2) and indicated that liver uptake in groups A and B was approximately twice that of group C. The data overall demonstrate a greater ability to concentrate product in the liver when Hp is present, either in a pre-formed complex with the modified Hb, or in the form of endogenous Hp where it is capable of forming a complex with administered Hb. There is also a clear indication that plasma retention of Hb conjugates is increased through combination with haptoglobin, such that a drug conjugate would be available for tissue uptake for a greater length of time.

TABLE 2

Areas under distribution curves for plasma and liver in rat.

| Group | AUC* (ug Hb · min/mL/dose) Plasma | AUC* (ug Hb · min/g/dose) Liver |
|---|---|---|
| A | 370.0 | 455.3 |
| B | 284.2 | 510.4 |
| C | 163.0 | 234.0 |

*dose = ug Hb/g body weight

Thus it has been demonstrated that agents can be conjugated to both 32 kDa hemoglobin dimer and to 64 kDa intramolecularly cross-linked Hb, using either attachment to side chain functionalities, to an intramolecular cross-linker or to a secondary linker attached to the intramolecular cross-linker. All of these constructs bound to haptoglobin. There has further been demonstrated the selective targeting of such a construct-complex, formed in vivo or ex vivo, to the liver and the extension of circulating half-life.

We claim:

1. A hemoglobin construct which binds to haptoglobin comprising a non-intramolecularly-cross-linked hemoglobin and a hepatocyte modifying substance bound to the hemoglobin.

2. A hemoglobin construct of claim 1 wherein the hemoglobin which binds to haptoglobin is both non-intramolecularly cross-linked and non-intermolecularly cross-linked.

3. The hemoglobin construct of claim 2 wherein the hepatocyte modifying substance is an agent which interacts with hepatocytes and consequently acts in vivo at the liver of a mammalian patient, and is selected from the group of substances consisting of diagnostic agents and markers.

4. The hemoglobin construct of claim 2 wherein the hepatocyte modifying substance is a therapeutic agent selected from the group consisting of: antineoplastic substances, antiviral substances, anti-inflammatory substances, anti-parasitic substances, anti-microbial substances, antioxidant substances, hepatoprotective agents, lipid metabolism agents, anti-toxicants, proteins and enzymes.

5. The hemoglobin construct of claim 2 wherein the hepatocyte modifying substance is putrescine.

6. The hemoglobin construct of claim 2 wherein the hepatocyte modifying substance is primaquine.

7. The hemoglobin construct of claim 2 wherein the hepatocyte modifying substance is a diagnostic agent.

8. The hemoglobin construct of claim 7 wherein the diagnostic agent is a radiolabelled compound or a fluorescent compound.

9. A method for diagnosing hepatic disorders in a mammalian patient which comprises administering to the patient an effective amount of the hemoglobin construct of claim 7 or 8.

10. The hemoglobin construct of claim 2 wherein the hemoglobin is a human hemoglobin.

11. A method for diagnosing hepatic disorders in a mammalian patient which comprises administering to the patient an effective amount of a hemoglobin construct of claim 2.

12. The hemoglobin construct of claim 2 wherein the hepatocyte modifying substance is bound to the hemoglobin through an intermediary of a chemical linker.

13. A hemoglobin construct-complex comprising the hemoglobin construct of claim 1 and heptoglobin bound to the hemoglobin portion thereof.

14. The hemoglobin construct-complex of claim 13 formed ex vivo by reacting the hemoglobin construct of claim 1 with the hepatocyte modifying substance and by reacting the haptoglobin with the hemoglobin.

15. The hemoglobin construct-complex of claim 13 wherein the hepatocyte modifying substance is an agent which interacts with hepatocytes and consequently acts in vivo at the liver of a mammalian patient, and is selected from the group of substances consisting of diagnostic agents and markers.

16. The hemoglobin construct-complex of claim 13 wherein the hepatocyte modifying substance is a therapeutic agent selected from the group consisting of antineoplastic substances, antiviral substances, anti-inflammatory substances, anti-parasitic substances, anti-microbial substances, antioxidant substances, hepatoprotective agents, lipid metabolism agents, anti-toxicants, proteins and enzymes.

17. The hemoglobin construct-complex of claim 13 wherein the hepatocyte modifying substance is putrescine.

18. The hemoglobin construct-complex of claim 13 wherein the hepatocyte modifying substance is primaquine.

19. The hemoglobin construct-complex of claim 13 wherein the hepatocyte modifying substance is a diagnostic agent.

20. The hemoglobin construct-complex of claim 19 wherein the diagnostic agent is a radiolabelled compound or a fluorescent compound.

21. A method for diagnosing hepatic disorders in a mammalian patient which comprises administering to the patient an effective amount of the hemoglobin construct-complex of claim 19 or 20.

22. The hemoglobin construct-complex of claim 13 wherein the hemoglobin is a human hemoglobin.

23. A method for diagnosing hepatic disorders in a mammalian patient which comprises administering to the patient an effective amount of a hemoglobin construct-complex of claim 13.

24. The hemoglobin construct-complex of claim 13 wherein the hepatocyte modifying substance is bound to the hemoglobin through an intermediary of a chemical linker.

25. The hemoglobin construct of claim 1 wherein the hepatocyte modifying substance is an agent which interacts with hepatocytes and consequently acts in vivo at the liver of a mammalian patient, and is selected from the group of substances consisting of diagnostic agents and markers.

26. The hemoglobin construct of claim 1 wherein the hepatocyte modifying substance is a therapeutic agent selected from the group consisting of: antineoplastic substances, antiviral substances, anti-inflammatory substances, anti-parasitic substances, anti-microbial substances, antioxidant substances, hepatoprotective agents, lipid metabolism agents, anti-toxicants, proteins and enzymes.

27. The hemoglobin construct of claim 1 wherein the hepatocyte modifying substance is putrescine.

28. The hemoglobin construct of claim 1 wherein the hepatocyte modifying substance is primaquine.

29. The hemoglobin construct of claim 1 wherein the hepatocyte modifying substance is a diagnostic agent.

30. The hemoglobin construct of claim 29 wherein the diagnostic agent is a radiolabelled compound or a fluorescent compound.

31. A method for diagnosing hepatic disorders in a mammalian patient which comprises administering to the patient an effective amount of the hemoglobin construct of claim 29 or 30.

32. The hemoglobin construct of claim 1 wherein the hemoglobin is a human hemoglobin.

33. A method for diagnosing hepatic disorders in a mammalian patient which comprises administering to the patient an effective amount of a hemoglobin construct of claim 1.

34. The hemoglobin construct of claim 1 wherein the hepatocyte modifying substance is bound to the hemoglobin through an intermediary of a chemical linker.

35. A hemoglobin construct-complex comprising the hemoglobin construct of claim 2 and heptoglobin bound to the hemoglobin portion thereof.

36. The hemoglobin construct-complex of claim 35 formed ex vivo by reacting the hemoglobin construct of claim 2 with the hepatocyte modifying substance and by reacting the haptoglobin with the hemoglobin.

37. The hemoglobin construct-complex of claim 35 wherein the hepatocyte modifying substance is an agent which interacts with hepatocytes and consequently acts in vivo at the liver of a mammalian patient, and is selected from the group of substances consisting of diagnostic agents and markers.

38. The hemoglobin construct-complex of claim 35 wherein the hepatocyte modifying substance is a therapeutic agent selected from the group consisting of antineoplastic substances, antiviral substances, anti-inflammatory substances, anti-parasitic substances, anti-microbial substances, antioxidant substances, hepatoprotective agents, lipid metabolism agents, anti-toxicants, proteins and enzymes.

39. The hemoglobin construct-complex of claim 35 wherein the hepatocyte modifying substance is putrescine.

40. The hemoglobin construct-complex of claim 35 wherein the hepatocyte modifying substance is primaquine.

41. The hemoglobin construct-complex of claim 35 wherein the hepatocyte modifying substance is a diagnostic agent.

42. The hemoglobin construct-complex of claim 41 wherein the diagnostic agent is a radiolabelled compound or a fluorescent compound.

43. A method for diagnosing hepatic disorders in a mammalian patient which comprises administering to the patient an effective amount of the hemoglobin construct-complex of claim 41 or 42.

44. The hemoglobin construct-complex of claim 35 wherein the hemoglobin is a human hemoglobin.

45. A method for diagnosing hepatic disorders in a mammalian patient which comprises administering to the patient an effective amount of a hemoglobin construct-complex of claim 35.

46. The hemoglobin construct-complex of claim 35 wherein the hepatocyte modifying substance is bound to the hemoglobin through an intermediary of a chemical linker.

47. A process for preparing a hemoglobin construct complex comprising reacting ex vivo a non-intramolecularly cross-linked hemoglobin with a hepatocyte modifying substance and reacting ex vivo the haptoglobin with the hemoglobin, wherein the haptoglobin and hepatocyte modifying substance are independently bound to the hemoglobin non-intramolecularly cross-linked.

48. A hemoglobin construct-complex prepared ex vivo comprising a non-intramolecularly cross-linked hemoglobin, haptoglobin bound to the hemoglobin and a hepatocyte modifying substance independently bound to the hemoglobin.

49. The hemoglobin construct-complex of claim 48 wherein the hepatocyte modifying substance is an agent which interacts with hepatocytes and consequently acts in vivo at the liver of a mammalian patient, and is selected from the group of substances consisting of diagnostic agents and markers.

50. The hemoglobin construct-complex of claim 48 wherein the hepatocyte modifying substance is a therapeutic agent selected from the group consisting of antineoplastic substances, antiviral substances, anti-inflammatory substances, anti-parasitic substances, anti-microbial substances, antioxidant substances, hepatoprotective agents, lipid metabolism agents, anti-toxicants, proteins and enzymes.

51. The hemoglobin construct-complex of claim 48 wherein the hepatocyte modifying substance is putrescine.

52. The hemoglobin construct-complex of claim 48 wherein the hepatocyte modifying substance is primaquine.

53. The hemoglobin construct-complex of claim 48 wherein the hepatocyte modifying substance is a diagnostic agent.

54. The hemoglobin construct-complex of claim 53 wherein the diagnostic agent is a radiolabelled compound or a fluorescent compound.

55. A method for diagnosing hepatic disorders in a mammalian patient which comprises administering to the patient an effective amount of the hemoglobin construct-complex of claim 53 or 54.

56. The hemoglobin construct-complex of claim 48 wherein the hemoglobin is a human hemoglobin.

57. A method for diagnosing hepatic disorders in a mammalian patient which comprises administering to the patient an effective amount of a hemoglobin construct-complex of claim 48.

58. The hemoglobin construct-complex of claim 40 wherein the hepatocyte modifying substance is bound to the hemoglobin through an intermediary of a chemical linker.

59. The hemoglobin construct-complex of claim 48 wherein the hepatocyte modifying substance is an agent which interacts with hepatocytes and consequently acts in vivo at the liver of a mammalian patient, and is selected from the group of substances consisting of diagnostic agents and markers.

60. The hemoglobin construct-complex of claim 59 wherein the hepatocyte modifying substance is a therapeutic agent selected from the group consisting of antineoplastic substances, antiviral substances, anti-inflammatory substances, anti-parasitic substances, anti-microbial substances, antioxidant substances, hepatoprotective agents, lipid metabolism agents, anti-toxicants, proteins and enzymes.

61. The hemoglobin construct-complex of claim 59 wherein the hepatocyte modifying substance is putrescine.

62. The hemoglobin construct-complex of claim 59 wherein the hepatocyte modifying substance is primaquine.

63. The hemoglobin construct-complex of claim 59 wherein the hepatocyte modifying substance is a diagnostic agent.

64. The hemoglobin construct-complex of claim 63 wherein the diagnostic agent is a radiolabelled compound or a fluorescent compound.

65. A method for diagnosing hepatic disorders in a mammalian patient which comprises administering to the patient an effective amount of the hemoglobin construct-complex of claim 63 or 64.

66. The hemoglobin construct-complex of claim 59 wherein the hemoglobin is a human hemoglobin.

67. A method for diagnosing hepatic disorders in a mammalian patient which comprises administering to the patient an effective amount of a hemoglobin construct-complex of claim 59.

68. A purified hemoglobin construct-complex comprising non-intromolecularly cross-linked hemoglobin prepared ex vivo represented by the general formula:

$$(Hp)_a\text{—}(Hb)_b\text{—}(L_c\text{—}A_d)_e$$

where
  a=1 to about 10
  b=0.5 to about 10
  c=0 to about 10
  d=1 to about 20
  e=1 to about 20
  Hp is haptoglobin
  Hb is hemoglobin
  L is a linker
  A is a hepatocyte modifying agent in which the stoichiometry of Hp to Hb in the complex is from about 1:0.5 to 1:2.

* * * * *